(12) United States Patent
Alhakimi et al.

(10) Patent No.: US 11,873,280 B2
(45) Date of Patent: *Jan. 16, 2024

(54) CROSS-LINKING AGENT(S)

(71) Applicant: GL CHEMTEC VISION INC., Oakville (CA)

(72) Inventors: Musa Alhakimi, Oakville (CA); Gamil Alhakimi, Oakville (CA); Lisa Studnicki, Oakville (CA)

(73) Assignee: GL CHEMTEC VISION INC., Oakville (CA)

( * ) Notice: Subject to any disclaimer, the term of this patent is extended or adjusted under 35 U.S.C. 154(b) by 138 days.

This patent is subject to a terminal disclaimer.

(21) Appl. No.: 17/143,297

(22) Filed: Jan. 7, 2021

(65) Prior Publication Data
US 2021/0130292 A1 May 6, 2021

Related U.S. Application Data

(63) Continuation of application No. 16/323,818, filed as application No. PCT/CA2017/050933 on Aug. 4, 2017, now Pat. No. 10,919,853.

(60) Provisional application No. 62/372,537, filed on Aug. 9, 2016.

(51) Int. Cl.
*C07D 207/277* (2006.01)
*G02C 7/04* (2006.01)
*A61L 27/52* (2006.01)
*A61L 27/18* (2006.01)
*C08F 220/26* (2006.01)
*C08F 220/34* (2006.01)
*C08K 5/3415* (2006.01)
*G02B 1/04* (2006.01)
*C08F 220/28* (2006.01)
*C08F 220/38* (2006.01)

(52) U.S. Cl.
CPC .......... *C07D 207/277* (2013.01); *A61L 27/18* (2013.01); *A61L 27/52* (2013.01); *C08F 220/26* (2013.01); *C08F 220/34* (2013.01); *C08K 5/3415* (2013.01); *G02B 1/043* (2013.01); *G02C 7/04* (2013.01); *A61L 2430/16* (2013.01); *C08F 220/283* (2020.02); *C08F 220/382* (2020.02); *C08F 2800/20* (2013.01)

(58) Field of Classification Search
CPC ..................................... G02B 1/043
See application file for complete search history.

(56) References Cited

U.S. PATENT DOCUMENTS

| | | | |
|---|---|---|---|
| 3,808,179 A | 4/1974 | Gaylord | |
| 4,910,277 A | 3/1990 | Bambury et al. | |
| 5,449,729 A | 9/1995 | Lai | |
| 8,242,224 B2 | 8/2012 | Hood et al. | |
| 8,937,110 B2 | 1/2015 | Alli et al. | |
| 10,919,853 B2 * | 2/2021 | Alhakimi | G02C 7/04 |
| 2004/0213827 A1 | 10/2004 | Enns et al. | |

FOREIGN PATENT DOCUMENTS

| | | |
|---|---|---|
| EP | 2042311 | 4/2009 |
| EP | 2042322 | 4/2009 |

OTHER PUBLICATIONS

Chan, G. Y. N. et al. (2000)—Approaches to the Controlled Formation of Network Polymers: 2. Studies of Hybrid Crosslinking Agents, Polymer, vol. 41, pp. 27-34.
Demirgöz, Döne et al. (2010)—Asymmetric Bihomologous Crosslinkers for Bicomponent Gels—The Way to Strongly Increased Elastic Moduli, Journal of Applied Polymers Science, vol. 115, pp. 896-900.
Gallardo, Alberto et al. (1999)—Micellar Electrokinetic Chromatography Applied to Copolymer Systems with Heterogeneous Distribution, Macromolecules, vol. 32, pp. 610-617.
Perrino, Monica et al. (2009)—"One-Pot" Synthesis of 1-Vinyl-2-Pyrrolidone with Protic Functional Groups in 3-Position, Macromolecular Chem Phys, vol. 210, pp. 1973-1978.
Tardjos, Myriam G et al. (2013)—Self-Structuring in Amphiphilic Networks Prepared by Single Conventional Radical Copolymerization of N-Butyl Methacrylate and Vinylpyrrolidone, Macromolecules, vol. 46, pp. 5018-5025.
Yu-Chin, Lai (1997)—A Novel Crosslinker for UV Copolymerization of N-vinyl Pyrrolidone and Methacrylates to Give Hydrogels, J. Polym Sci A: Polym Chem, vol. 35, pp. 1039-1046.
International Preliminary Report on Patentability dated Feb. 21, 2019 on PCT/CA2017/050933.

* cited by examiner

*Primary Examiner* — Michael F Pepitone
(74) *Attorney, Agent, or Firm* — Thomas | Horstemeyer, LLP

(57) ABSTRACT

Cross-linking agent(s), composition(s) made therefrom and use(s) thereof. For example, crosslinking agent(s) that are used to make composition(s) such as hydrogel material(s). Such materials are useful in the manufacture of biocompatible medical devices, for example, hydrogel materials having desirable physical properties for use as contact lense(s) and/or stimulating device(s).

47 Claims, No Drawings

CROSS-LINKING AGENT(S)

CROSS-REFERENCE TO RELATED APPLICATION

This application is a continuation of U.S. application Ser. No. 16/323,818, filed Feb. 7, 2019, now U.S. Pat. No. 10,919,853 issued Feb. 16, 2021. U.S. application Ser. No. 16/323,818 is the 35 U.S.C. § 371 national stage application of PCT Application No. PCT/CA2017/050933, filed Aug. 4, 2017, where the PCT claims the priority to and benefit of U.S. Provisional Patent Application No. 62/372,537, filed Aug. 9, 2016. Each of these applications is incorporated herein by reference in their entireties.

FIELD

The subject application relates generally to cross-linking agent(s), composition(s) made therefrom and use(s) thereof. For example, the application is directed to crosslinking agent(s) that are used to make composition(s) such as hydrogel material(s). Such materials are useful in the manufacture of biocompatible medical devices, for example, hydrogel materials, which include silicon hydrogels, having desirable physical properties for use as contact lense(s) and/or stimulating device(s).

BACKGROUND

Hydrogels are hydrophilic polymers that absorb water, and are essentially insoluble in water at physiologic temperature, pH, and ionic strength due to the presence of a three-dimensional polymeric network. While hydrogel are prepared from hydrophilic monomers, hydrophobic monomer are sometimes used in hydrogel preparation in order to regulate the properties of specific applications. The three-dimensional network includes crosslinks between polymer chains of the network, and these crosslinks can be formed by covalent bonds, electrostatic, hydrophobic, or dipole-dipole interactions. The hydrophilicity of the hydrogel materials is in large part due to the presence of hydrophilic groups, in some instances, along the polymer backbone, and in other instances, as functional side groups that extend from the polymer backbone. Generally, a hydrogel is a crosslinked polymer that absorbs water to an equilibrium value of at least 10% water. The water-swollen equilibrated state of a hydrogel results from a balance between an osmotic force that drives the water to enter the hydrophilic polymer network, and a cohesive force exerted by the polymer chains in resisting expansion. In some fashion, both the osmotic force and the cohesive force correlates with the type of monomers used to prepare the hydrogel polymeric material and the crosslink density of the polymeric hydrogel material. In general, a person of ordinary skill would expect a greater degree of crosslinking for a given hydrogel polymeric material will result in a corresponding decrease in water content, i.e., at equilibrium, the weight percentage of water absorbed by the polymeric network under physiological conditions relative to its total (dry plus water) weight. Water content (%) is simply {[wet lens (g)–dry lens (g)]/wet lens (g)}×100 at equilibrium.

Hydrogels can be classified as synthetic or natural according to their origin; degradable or stable depending on their stability characteristics, and intelligent or conventional depending on their ability to exhibit significant dimensional changes with variations in pH, temperature or electric field. One class of conventional synthetic hydrogels is prepared by free-radical polymerization of vinyl or (meth)acrylate monomers using thermal or photo initiators. Several important classes of monomers are recognized by persons of skill with an interest to prepare hydrogel polymeric materials. There are the neutral monomers, for example, methacrylates and acrylates, e.g., 2-hydroxyethyl methacrylate (HEMA), acrylamide/methacrylamides, e.g., dimethyl acrylamide (DMA), glycerol methacrylate (GMA) and cyclic lactams, e.g., N-vinyl-2-pyrrolidone (NVP). At times, the term N-vinylpyrrolidone is used interchangeably with N-vinyl-2-pyrrolidone, and both chemical terms are well recognized by persons of ordinary skill to mean the same vinyl monomer. Another class of monomers is the ionic or charged (under physiological conditions) monomers, including, methacrylic acid, acrylic acid, methylpropylsulfonic acid and p-styrene sulfonate. Typically, in the making of contact lenses the ionic class of monomer is present at low concentration relative to the neutral class of monomer, but the former can have a dramatic effect on water content of the material. For example, copolymerization of 2% w/w methacrylic acid with HEMA results in a hydrogel possessing a water content of 60% (compared with 38% water content for HEMA alone). As used herein "(meth)" refers to an optional methyl substitution. Thus, a term such as "(meth)acrylate" denotes both methacrylic and acrylic radicals.

Hydrogel materials prepared with vinyl cyclic lactams. e.g., N-vinyl-2-pyrrolidone (NVP) can have relatively high water content, and thus, an acceptable level of oxygen permeability. For example, NVP is often copolymerized with an alkyl acrylate or methacrylate such as methyl methacrylate to provide lens materials that typically have a water content of 50% to 80% by weight. However, such copolymers are difficult to synthesize in a controlled manner because of the difference in their respective rates of polymerization between the N-vinyl groups of NVP and the acryloyl or methacryloyl groups of the alkyl acrylate or methacrylate. During free-radical polymerization, the methacrylate monomers polymerize relatively quickly while the vinyl cyclic lactam monomer polymerize more slowly, and therefore, only small amounts of the two co-monomers actually react with the other. What one finds is that the polymer network is essentially an interpenetrating network of poly(vinyl monomer) and poly((meth)acrylate)). The result is often a phase separation and a corresponding decrease in the transparency of the polymeric lens material, or the mechanical properties of the lens material deteriorates as the lens absorbs water.

It is also observed, and not to be overlooked, that in a conventional poly(vinyl monomer) and poly((meth)acrylate)) hydrogel framework a minimum of crosslinking occurs between the two essentially homopolymers. In the absence of a suitable crosslinking agent to link the two dual phase polymers, high levels of extractables and dimensional instability results. There have been attempts to design cross-linking agents that address this technical issue. See, U.S. Pat. No. 5,449,729 (Lai, et al), which discloses the use of a crosslinking agent containing both methacrylate and vinyl carbonate reactivity. However, technical issues such as cost to synthesize, toxic preparatory chemistry as well as the relative instability of the vinyl carbonate functionality has limited the development of this dual reactive cross-linking agent(s).

There have been attempts to prepare high water content hydrogels using two different cross-linking agent(s), i.e., allyl methacrylate (AMA) or divinylethylene urea (DVEU), to incorporate the vinyl (cyclic lactam) monomer into the hydrogel polymer network. The AMA cross-linking agent(s)

works quite well with monomers systems where a fast polymerizing (meth)acrylate are used and leaves the slow polymerizable NVP intact. The technical issue with AMA is that it is too volatile and can volatilize during the thermal cure of the polymer resulting in inconsistent levels of crosslinking from one polymerization to the next. Also, DVEU is not an optimal crosslinking agent because it possesses tow vinyl group with the same reactivity on the same molecule, and seems to limit the mobility of the poly(NVP) within the hydrogel framework. For example, as films or lenses are being made, or as water enters the framework, the resulting hydrogel material can exhibit loss of lubricity at the surface of the hydrogel. For application of a contact lens, the loss of lubricity is believed to be detrimental to the sensed comfort a consumer will experience in wearing the lens.

Silicone hydrogels combine the high oxygen permeability of polydimethylsiloxane and the excellent water absorption characteristics of a hydrogel. However, for the application of a contact lens, one well known issue with preparing silicone hydrogels is that silicone based monomers are hydrophobic, and relatively, incompatible in regards to forming a homogeneous polymerization mixture with the hydrophilic monomers present in the mixture. The copolymerization of (meth)acrylate functionalized silicones with hydrophilic monomers generally results in opaque, phase separated materials. Technical approaches to minimize such mix incompatibility can include the use of a solubilizing co-solvent or incorporating hydrophilic groups to the silicone backbone.

There is still a need for components and/or materials useful for making biocompatible medical devices that have desired physical properties.

SUMMARY

In accordance with an aspect, there is a compound of formula I:

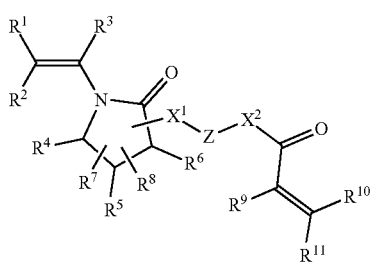

(I)

$R^1$-$R^{11}$ are the same or different, and are each independently selected from H, halo, hydroxyl, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, a substituted or unsubstituted heteroaromatic group, or $NR^aR^b$, wherein $R^a$ and $R^b$ are the same or different, and are independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group;

$X^1$ and $X^2$ are the same or different, and are each independently selected from a direct bond, a heteroatom, C(O), a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, a substituted or unsubstituted heteroaromatic group, or $NR^a$; and Z is selected from a heteroatom, C(O), a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, a substituted or unsubstituted heteroaromatic group, $NR^a$, or $[SiR^{12}R^{13}O]_wSiR^{12}R^{13}$, wherein $R^{12}$ and $R^{13}$ are the same or different, and are independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and w is from 0 to 60.

In another aspect, there is provided a compound of formula II:

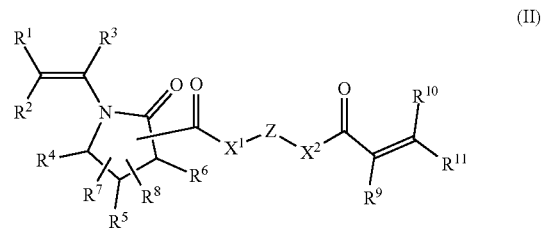

(II)

$R^1$-$R^{11}$ are the same or different, and are each independently selected from H, halo, hydroxyl, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, a substituted or unsubstituted heteroaromatic group, or $NR^aR^b$, wherein $R^a$ and $R^b$ are the same or different, and are independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group;

$X^1$ and $X^2$ are the same or different, and are each independently selected from a direct bond, a heteroatom, C(O), a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, a substituted or unsubstituted heteroaromatic group, or $NR^a$; and Z is selected from a heteroatom, C(O), a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, a substituted or unsubstituted heteroaromatic group, $NR^a$, or $[SiR^{12}R^{13}O]_wSiR^{12}R^{13}$, wherein $R^{12}$ and $R^{13}$ are the same or different, and are independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and w is from 0 to 60.

In other aspects described herein, wherein $R^1$-$R^{11}$ are the same or different, and are each independently selected from H, halo, hydroxyl, a substituted or unsubstituted hydrocarbon group, or a substituted or unsubstituted heterogeneous group. In further aspects, wherein $R^1$-$R^{11}$ are the same or different, and are each independently selected from H, halo, hydroxyl, a substituted or unsubstituted $C_1$-$C_6$ alkyl, a substituted or unsubstituted $C_1$-$C_6$ alkoxy, or a substituted or unsubstituted $C_1$-$C_6$ alkanol. In other aspects, wherein $R^1$-$R^{11}$ are the same or different, and are each independently selected from H or a substituted or unsubstituted hydrocarbon group. In further aspects, wherein $R^1$-$R^{11}$ are the same or different, and are each independently selected from H or a substituted or unsubstituted alkyl group. In other aspects, wherein $R^1$-$R^{11}$ are the same or different, and are each independently selected from H or a substituted or unsubstituted $C_1$-$C_6$ alkyl. In yet other aspects, wherein $R^1$-$R^{11}$ are the same or different, and are each independently selected from H or unsubstituted $C_1$-$C_6$ alkyl. In further aspects wherein $R^1$-$R^{11}$ are the same or different, and are each independently selected from H or methyl. In other aspects, wherein $R^1$, $R^2$, $R^{10}$, and $R^{11}$ are H.

In other aspects described herein, wherein $X^1$ and $X^2$ are the same or different, and are each independently selected from a direct bond, O, $NR^a$, C(O), C(O)$NR^a$, $NR^a$C(O), OC(O)$NR^a$, $NR^a$C(O)O, $NR^a$C(O)NH, NHC(O)$NR^a$, C(O)O, OC(O), NHC(O)NHZ$_0$—NH—C(O)NH, OC(O)NHZ$_0$—NH—C(O)O, OC(O)NHZ$_0$—NH—C(O)NH, or NHC(O)NHZ$_0$—NH—C(O)O; where $Z_0$ is a linear or branched $C_2$-$C_{12}$ alkylene divalent radical, or a $C_5$-$C_7$ cycloaliphatic divalent radical, each of which can optionally include one or more linkages of O, $NR^a$ and C(O). In further aspects, wherein $X^1$ and $X^2$ are the same or different, and are each independently selected from a direct bond, O, $NR^a$, C(O), C(O)$NR^a$, $NR^a$C(O), $NR^a$C(O), OC(O)$NR^a$, $NR^a$C(O)O, C(O)O, or OC(O). In other aspects, wherein $R^a$ is selected from H or a substituted or unsubstituted hydrocarbon group. In further aspects, wherein $R^a$ is selected from H or unsubstituted $C_1$-$C_6$ alkyl. In other aspects, wherein $R^a$ is selected from H or methyl. In further aspects, wherein $X^1$ and $X^2$ are the same or different, and are each independently selected from a direct bond, O, or $NR^a$.

In other aspects described herein, wherein Z is selected from a direct bond, a substituted or unsubstituted hydrocarbon group, a substituted or unsubstituted heterogeneous group, or $[SiR^{12}R^{13}O]_wSiR^{12}R^{13}$. In other aspects, wherein Z is selected from a direct bond, a substituted or unsubstituted hydrocarbon group, a substituted or unsubstituted heterogeneous group, or $[SiR^{12}R^{13}O]_wSiR^{12}R^{13}$, wherein $R^{12}$ and $R^{13}$ are the same or different, and are independently selected from $C_1$-$C_4$ alkyl or phenyl, and w is from 0 to 60. In further aspects, wherein Z is selected from a direct bond, or a substituted or unsubstituted hydrocarbon group. In other aspects, wherein Z is selected from a substituted or unsubstituted hydrocarbon group. In further aspects, wherein Z is selected from a substituted or unsubstituted alkyl group. In other aspects, wherein Z is selected from a substituted or unsubstituted $C_1$-$C_{20}$ alkyl. In further aspects, wherein Z is selected from a substituted or unsubstituted $C_1$-$C_6$ alkyl. In other aspects, wherein Z is selected from an unsubstituted $C_1$-$C_6$ alkyl. In further aspects, wherein Z is selected from a substituted or unsubstituted aromatic group. In other aspects, wherein Z is selected from a substituted or unsubstituted phenyl group. In further aspects, wherein Z is selected from a $C_1$-$C_{12}$ unsubstituted or substituted, linear or branched alkylene divalent radical, where each alkylene divalent radical can optionally include one or more linkages of O, $NR^a$, and C(O), an unsubstituted phenylene divalent radical, a $C_5$-$C_7$ cycloaliphatic divalent radical, or a $C_7$-$C_{12}$ arylalkylene divalent radical.

In other aspects described herein, wherein the compound is Formula III

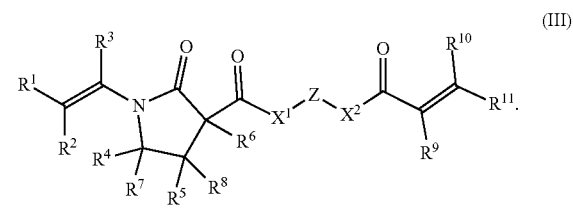

In other aspects described herein, wherein the compound is selected from one or more of

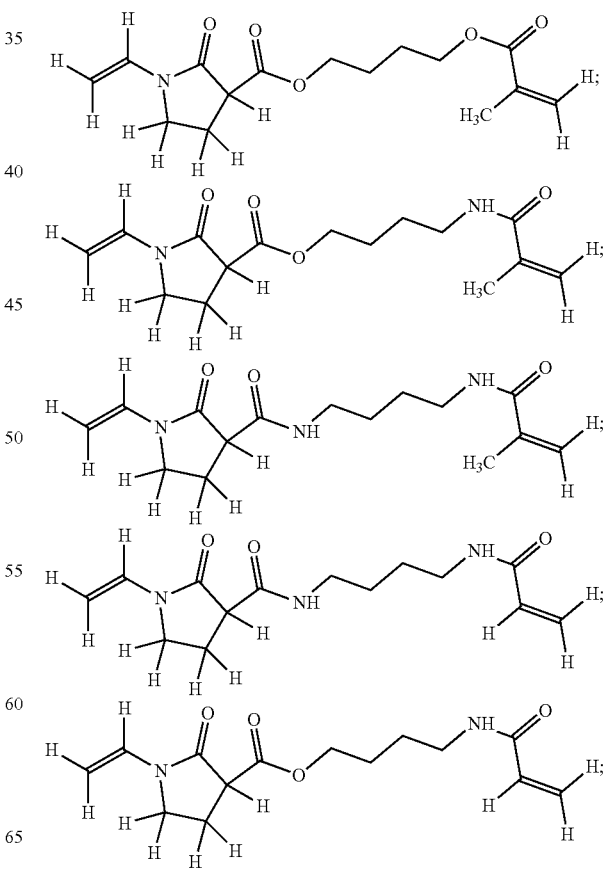

-continued

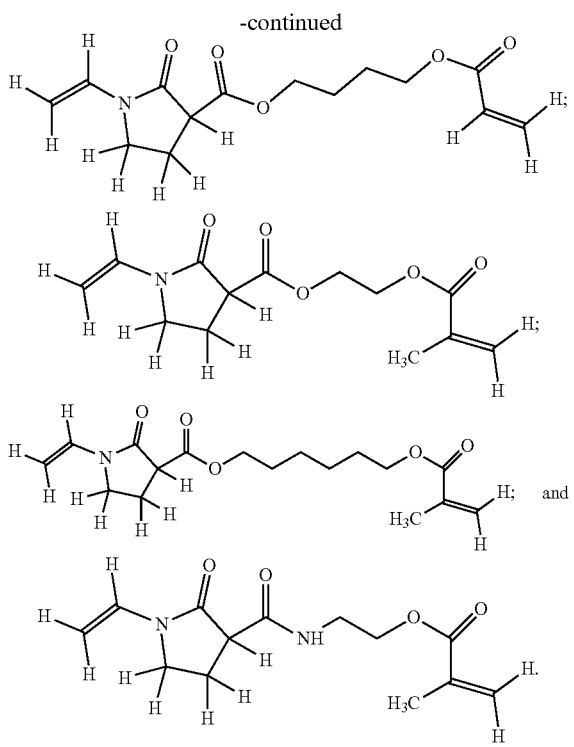

In other aspects described herein, wherein —$X^1$—Z—$X^2$— is not —$CH_2$—$CH_2$—O—C(O)—.

In other aspects described herein, wherein the compound is not

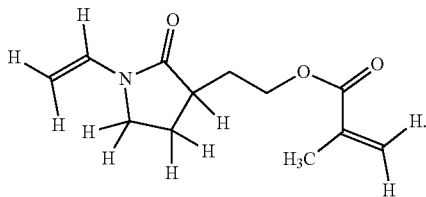

In other aspects described herein, wherein the compound is a dual reactive cross-linking agent(s).

In other aspects described herein, there is provided a composition comprising one or more of the compounds defined herein.

In other aspects described herein, there is provided use of one or more of the compounds defined herein.

In other aspects described herein, there is provided use of one or more of the compounds defined herein to produce biocompatible medical devices(s).

In other aspects described herein, there is provided a method of producing biocompatible medical devices(s), the method comprising reacting at least one of the compounds defined herein with at least one monomer.

In other aspects described herein, there is provided a composition comprising at least one (meth)acrylic monomer, at least one vinyl containing monomer and at least one of the compounds as defined herein.

In other aspects described herein, wherein the at least one vinyl containing monomer comprises at least one silicone monomer. In other aspects, wherein the silicone monomer is selected from the group consisting of tris-(trimethylsiloxy)-3-methacryloxypropyl methacrylate (Tris), 3-methacryloxy-2-hydroxypropyloxy) propylbis(trimethylsiloxy)-methylsilane (Sigma), or a mixture thereof. In further aspects, wherein the at least one vinyl containing monomer is selected from hydroxyethylmethacrylate (HEMA), glycidyl methacrylate (GMMA), dimethylacrylamide (DMA), 3-(tris-(trimethylsiloxy)silyl)propyl methacrylate (TRIS), hydroxypropyloxy)propylbis(trimethylsiloxy) methylsilane (SIGMA), or combinations thereof. In other aspects, wherein the at least one vinyl monomer is selected from N-vinyl-2-pyrrolidone, N-vinyl piperidone, N-vinyl-caprolactam, N-vinylimidazolidone, N-vinylsuccinimide, N-vinylformamide, N-vinyl urea, N-vinylcarbamate, O-vinyl carbonate, or combinations thereof. In further aspects, wherein the at least one (meth)acrylic monomer includes 4-t-butyl-2-hydroxycyclohexylmethacrylate, and the at least one vinyl monomer includes N-vinyl-2-pyrrolidone. In other aspects, wherein the at least one (meth)acrylic monomer includes a functional monomer selected from the group consisting of carboxybetaines, sulfobetains and phosphobetaines. In other aspects, wherein the functional monomer is selected from the group consisting of methacryloxy phosphatidyl choline (MPC), N-vinylcarboxy ethyl phosphatidyl choline, O-vinyl ethyl phosphatidyl choline carbonate, 1-(3-sulfopropyl)-2-vinylpyridinium betaine, and 3-dimethyl (acryloyloxyethyl) ammonium propyl sulfonate. In other aspects, further comprising at least one photoinitiator. In further aspects, further comprising at least one (meth)acrylate cross-linking agent. In other aspects, wherein the Tris, Sigma or the combination thereof is present from about 8% to about 30% by weight. In further aspects, wherein the at least one compound is present from about 0.02% to about 0.4% by weight.

In other aspects described herein, there is provided a hydrogel polymer prepared from the composition described herein. In other aspects, wherein the polymer possesses a water content of at least about 40% by weight, at least about 45% by weight, at least about 50% by weight, at least about 65% by weight, at least about 70% by weight, at least about 71% by weight, at least about 77% by weight, or at least about 80% by weight. In further aspects, wherein the polymer possesses a modulus of elasticity of at least about 0.30 MPa, at least about 0.35 MPa, at least about 0.40 MPa, or at least about 0.45 MPa.

In other aspects described herein, there is provided a contact lens prepared with the hydrogel polymer described herein.

Other features and advantages of the present invention will become apparent from the following detailed description. It should be understood, however, that the detailed description and the specific examples while indicating embodiments of the invention are given by way of illustration only, since various changes and modifications within the spirit and scope of the invention will become apparent to those skilled in the art from the detailed description.

DETAILED DESCRIPTION OF CERTAIN EMBODIMENTS

Definitions

When describing the compounds, compositions, methods and uses of this invention, the following terms have the following meanings unless otherwise indicated.

The compounds of the present invention may have asymmetric centers, chiral axes, and chiral planes (as described, for example, in: E. L. Eliel and S. H. Wilen, Stereochemistry of Carbon Compounds, John Wiley & Sons, New York, 1994, pages 1119-1190), and occur as racemates, racemic mixtures, and as individual diastereomers, with all possible isomers and mixtures thereof, including optical isomers, E isomers, and Z isomers, being included in the present invention. In addition, the compounds disclosed herein may exist as tautomers and both tautomeric forms are intended to be encompassed by the scope of the invention, even though only one tautomeric structure may be depicted.

Generally, reference to a certain element such as hydrogen or H is meant to, if appropriate, include all isotopes of that element.

Where the term "alkyl group" is used, either alone or within other terms such as "haloalkyl group" and "alkylamino group", it encompasses linear or branched carbon radicals having, for example, one to about twenty carbon atoms or, in specific embodiments, one to about twelve carbon atoms. In other embodiments, alkyl groups are "lower alkyl" groups having one to about six carbon atoms. Examples of such groups include, but are not limited thereto, methyl, ethyl, n-propyl, isopropyl, n-butyl, isobutyl, sec-butyl, tert-butyl, pentyl, iso-amyl, hexyl and the like. In more specific embodiments, lower alkyl groups have one to four carbon atoms.

The term "alkenyl group" encompasses linear or branched carbon radicals having at least one carbon-carbon double bond. The term "alkenyl group" can encompass conjugated and non-conjugated carbon-carbon double bonds or combinations thereof. An alkenyl group, for example and without being limited thereto, can encompass two to about twenty carbon atoms or, in a particular embodiment, two to about twelve carbon atoms. In embodiments, alkenyl groups are "lower alkenyl" groups having two to about four carbon atoms. Examples of alkenyl groups include, but are not limited thereto, ethenyl, propenyl, allyl, propenyl, butenyl and 4-methylbutenyl. The terms "alkenyl group" and "lower alkenyl group", encompass groups having "cis" and "trans" orientations, or alternatively, "E" and "Z" orientations.

The term "alkynyl group" denotes linear or branched carbon radicals having at least one carbon-carbon triple bond. The term "alkynyl group" can encompass conjugated and non-conjugated carbon-carbon triple bonds or combinations thereof. Alkynyl group, for example and without being limited thereto, can encompass two to about twenty carbon atoms or, in a particular embodiment, two to about twelve carbon atoms. In embodiments, alkynyl groups are "lower alkynyl" groups having two to about ten carbon atoms. Some examples are lower alkynyl groups having two to about four carbon atoms. Examples of such groups include propargyl, butynyl, and the like.

The term "halo" means halogens such as fluorine, chlorine, bromine or iodine atoms.

The term "haloalkyl group" encompasses groups wherein any one or more of the alkyl carbon atoms is substituted with halo as defined above. Specifically encompassed are monohaloalkyl, dihaloalkyl and polyhaloalkyl groups including perhaloalkyl. A monohaloalkyl group, for one example, may have either an iodo, bromo, chloro or fluoro atom within the group. Dihalo and polyhaloalkyl groups may have two or more of the same halo atoms or a combination of different halo groups. "Lower haloalkyl group" encompasses groups having 1-6 carbon atoms. In some embodiments, lower haloalkyl groups have one to three carbon atoms. Examples of haloalkyl groups include fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The term "hydroxyalkyl group" encompasses linear or branched alkyl groups having, for example and without being limited thereto, one to about ten carbon atoms, any one of which may be substituted with one or more hydroxyl groups. In embodiments, hydroxyalkyl groups are "lower hydroxyalkyl" groups having one to six carbon atoms and one or more hydroxyl groups. Examples of such groups include hydroxymethyl, hydroxyethyl, hydroxypropyl, hydroxybutyl and hydroxyhexyl.

The term "alkoxy group" encompasses linear or branched oxy-containing groups each having alkyl portions of, for example and without being limited thereto, one to about ten carbon atoms. In embodiments, alkoxy groups are "lower alkoxy" groups having one to six carbon atoms. Examples of such groups include methoxy, ethoxy, propoxy, butoxy and tert-butoxy. In certain embodiments, lower alkoxy groups have one to three carbon atoms. The "alkoxy" groups may be further substituted with one or more halo atoms, such as fluoro, chloro or bromo, to provide "haloalkoxy" groups. In other embodiments, lower haloalkoxy groups have one to three carbon atoms. Examples of such groups include fluoromethoxy, chloromethoxy, trifluoromethoxy, trifluoroethoxy, fluoroethoxy, and fluoropropoxy.

The term "aromatic group" or "aryl group" means an aromatic group having one or more rings wherein such rings may be attached together in a pendent manner or may be fused. In particular embodiments, an aromatic group is one, two or three rings. Monocyclic aromatic groups may contain 4 to 10 carbon atoms, typically 4 to 7 carbon atoms, and more typically 4 to 6 carbon atoms in the ring. Typical polycyclic aromatic groups have two or three rings. Polycyclic aromatic groups having two rings typically have 8 to 12 carbon atoms, typically 8 to 10 carbon atoms in the rings. Examples of aromatic groups include, but are not limited to, phenyl, naphthyl, tetrahydronaphthyl, indanyl, biphenyl, phenanthryl, anthryl or acenaphthyl.

The term "heteroatom" means an atom other than carbon. Typically, heteroatoms are selected from the group consisting of sulfur, phosphorous, nitrogen and oxygen atoms. Groups containing more than one heteroatom may contain different heteroatoms.

The term "heteroaromatic group" or "heteroaryl group" means an aromatic group having one or more rings wherein such rings may be attached together in a pendent manner or may be fused, wherein the aromatic group has at least one heteroatom. Monocyclic heteroaromatic groups may contain 4 to 10 member atoms, typically 4 to 7 member atoms, and more typically 4 to 6 member atoms in the ring. Typical polycyclic heteroaromatic groups have two or three rings. Polycyclic aromatic groups having two rings typically have 8 to 12 member atoms, more typically 8 to 10 member atoms in the rings. Examples of heteroaromatic groups include, but are not limited thereto, pyrrole, imidazole, thiazole, oxazole, furan, thiophene, triazole, pyrazole, isoxazole, isothiazole, pyridine, pyrazine, pyridazine, pyrimidine, triazine, indole, benzofuran, benzothiophene, benzimidazole, benzthiazole, quinoline, isoquinoline, quinazoline, quinoxaline and the like.

The term "carbocyclic group" means a saturated or unsaturated carbocyclic hydrocarbon ring. Carbocyclic groups are not aromatic. Carbocyclic groups are monocyclic or polycyclic. Polycyclic carbocyclic groups can be fused, spiro, or bridged ring systems. Monocyclic carbocyclic groups may contain 4 to 10 carbon atoms, typically 4 to 7 carbon atoms, and more typically 5 to 6 carbon atoms in the ring. Bicyclic carbocyclic groups may contain 8 to 12 carbon atoms, typically 9 to 10 carbon atoms in the rings.

The term "heterocyclic group" means a saturated or unsaturated ring structure containing carbon atoms and 1 or more heteroatoms in the ring. Heterocyclic groups are not aromatic. Heterocyclic groups are monocyclic or polycyclic. Polycyclic heterocyclic groups can be fused, spiro, or bridged ring systems. Monocyclic heterocyclic groups may contain 4 to 10 member atoms (i.e., including both carbon atoms and at least 1 heteroatom), typically 4 to 7, and more typically 5 to 6 in the ring. Bicyclic heterocyclic groups may contain 8 to 18 member atoms, typically 9 or 10 member atoms in the rings. Representative heterocyclic groups include, by way of example, pyrrolidine, imidazolidine, pyrazolidine, piperidine, 1,4-dioxane, morpholine, thiomorpholine, piperazine, 3-pyrroline and the like.

The term "heterogeneous group" means a saturated or unsaturated chain of non-hydrogen member atoms comprising carbon atoms and at least one heteroatom. Heterogeneous groups typically have 1 to 25 member atoms. More typically, the chain contains 1 to 12 member atoms, 1 to 10, and most typically 1 to 6. The chain may be linear or branched. Typical branched heterogeneous groups have one or two branches, more typically one branch. Typically, heterogeneous groups are saturated. Unsaturated heterogeneous groups may have one or more double bonds, one or more triple bonds, or both. Typical unsaturated heterogeneous groups have one or two double bonds or one triple bond. More typically, the unsaturated heterogeneous group has one double bond.

The term "hydrocarbon group" or "hydrocarbyl group" means a chain of 1 to 25 carbon atoms, typically 1 to 12 carbon atoms, more typically 1 to 10 carbon atoms, and most typically 1 to 8 carbon atoms. Hydrocarbon groups may have a linear or branched chain structure. Typical hydrocarbon groups have one or two branches, typically one branch. Typically, hydrocarbon groups are saturated. Unsaturated hydrocarbon groups may have one or more double bonds, one or more triple bonds, or combinations thereof. Typical unsaturated hydrocarbon groups have one or two double bonds or one triple bond; more typically unsaturated hydrocarbon groups have one double bond.

When the term "unsaturated" is used in conjunction with any group, the group may be fully unsaturated or partially unsaturated. However, when the term "unsaturated" is used in conjunction with a specific group defined herein, the term maintains the limitations of that specific group. For example, an unsaturated "carbocyclic group", based on the limitations of the "carbocyclic group" as defined herein, does not encompass an aromatic group.

The terms "carboxy group" or "carboxyl group", whether used alone or with other terms, such as "carboxyalkyl group", denotes —(C=O)—O— or C(O)O.

The term "carbonyl group", whether used alone or with other terms, such as "aminocarbonyl group", denotes —(C=O)— or C(O) The terms "alkylcarbonyl group" denotes carbonyl groups which have been substituted with an alkyl group. In certain embodiments, "lower alkylcarbonyl group" has lower alkyl group as described above attached to a carbonyl group.

The term "aminoalkyl group" encompasses linear or branched alkyl groups having one to about ten carbon atoms any one of which may be substituted with one or more amino groups. In some embodiments, the aminoalkyl groups are "lower aminoalkyl" groups having one to six carbon atoms and one or more amino groups. Examples of such groups include aminomethyl, aminoethyl, aminopropyl, aminobutyl and aminohexyl.

The term "alkylaminoalkyl group" encompasses aminoalkyl groups having the nitrogen atom independently substituted with an alkyl group. In certain embodiments, the alkylaminoalkyl groups are "loweralkylaminoalkyl" groups having alkyl groups of one to six carbon atoms. In other embodiments, the lower alkylaminoalkyl groups have alkyl groups of one to three carbon atoms. Suitable alkylaminoalkyl groups may be mono or dialkyl substituted, such as N-methylaminomethyl, N, N-dimethyl-aminoethyl, N, N-diethylaminomethyl and the like.

The term "aralkyl group" encompasses aryl-substituted alkyl groups. In embodiments, the aralkyl groups are "lower aralkyl" groups having aryl groups attached to alkyl groups having one to six carbon atoms. In other embodiments, the lower aralkyl groups phenyl is attached to alkyl portions having one to three carbon atoms. Examples of such groups include benzyl, diphenylmethyl and phenylethyl. The aryl in said aralkyl may be additionally substituted with halo, alkyl, alkoxy, haloalkyl and haloalkoxy.

The term "arylalkenyl group" encompasses aryl-substituted alkenyl groups. In embodiments, the arylalkenyl groups are "lower arylalkenyl" groups having aryl groups attached to alkenyl groups having two to six carbon atoms. Examples of such groups include phenylethenyl. The aryl in said arylalkenyl may be additionally substituted with halo, alkyl, alkoxy, haloalkyl and haloalkoxy.

The term "arylalkynyl group" encompasses aryl-substituted alkynyl groups. In embodiments, arylalkynyl groups are "lower arylalkynyl" groups having aryl groups attached to alkynyl groups having two to six carbon atoms. Examples of such groups include phenylethynyl. The aryl in said aralkyl may be additionally substituted with halo, alkyl, alkoxy, haloalkyl and haloalkoxy. The terms benzyl and phenylmethyl are interchangeable.

The term "alkylthio group" encompasses groups containing a linear or branched alkyl group, of one to ten carbon atoms, attached to a divalent sulfur atom. In certain embodiments, the lower alkylthio groups have one to three carbon atoms. An example of "alkylthio" is methylthio, ($CH_3S$—).

The term "alkylamino group" denotes amino groups which have been substituted with one alkyl group and with two alkyl groups, including terms "N-alkylamino" and "N,N-dialkylamino". In embodiments, alkylamino groups are "lower alkylamino" groups having one or two alkyl groups of one to six carbon atoms, attached to a nitrogen atom. In other embodiments, lower alkylamino groups have one to three carbon atoms. Suitable "alkylamino" groups may be mono or dialkylamino such as N-methylamino, N-ethylamino, N,N-dimethylamino, N,N-diethylamino and the like.

The term "arylamino group" denotes amino groups which have been substituted with one or two aryl groups, such as N-phenylamino. The "arylamino" groups may be further substituted on the aryl ring portion of the group.

The term "heteroarylamino" denotes amino groups which have been substituted with one or two heteroaryl groups, such as N-thienylamino. The "heteroarylamino" groups may be further substituted on the heteroaryl ring portion of the group.

The term "aralkylamino group" denotes amino groups which have been substituted with one or two aralkyl groups. In other embodiments, there are phenyl-$C_1$-$C_3$-alkylamino groups, such as N-benzylamino. The "aralkylamino" groups may be further substituted on the aryl ring portion of the group.

The term "alkylaminoalkylamino group" denotes alkylamino groups which have been substituted with one or two alkylamino groups. In embodiments, there are $C_1$-$C_3$-alkylamino-$C_1$-$C_3$-alkylamino groups.

The term "arylthio group" encompasses aryl groups of six to ten carbon atoms, attached to a divalent sulfur atom. An example of "arylthio" is phenylthio. The term "aralkylthio group" encompasses aralkyl groups as described above, attached to a divalent sulfur atom. In certain embodiments there are phenyl-$C_1$-$C_3$-alkylthio groups. An example of "aralkylthio" is benzylthio.

The term "aryloxy group" encompasses optionally substituted aryl groups, as defined above, attached to an oxygen atom. Examples of such groups include phenoxy.

The term "aralkoxy group" encompasses oxy-containing aralkyl groups attached through an oxygen atom to other groups. In certain embodiments, aralkoxy groups are "lower aralkoxy" groups having optionally substituted phenyl groups attached to lower alkoxy group as described above.

The term "cycloalkyl group" includes saturated carbocyclic groups. In certain embodiments, cycloalkyl groups include $C_3$-$C_6$ rings. In embodiments, there are compounds that include, cyclopentyl, cyclopropyl, and cyclohexyl.

The term "cycloalkenyl group" includes carbocyclic groups that have one or more carbon-carbon double bonds; conjugated or non-conjugated, or a combination thereof. "Cycloalkenyl" and "cycloalkyldienyl" compounds are included in the term "cycloalkenyl". In certain embodiments, cycloalkenyl groups include $C_3$-$C_6$ rings. Examples include cyclopentenyl, cyclopentadienyl, cyclohexenyl and cycloheptadienyl. The "cycloalkenyl" group may have 1 to 3 substituents such as lower alkyl, hydroxyl, halo, haloalkyl, nitro, cyano, alkoxy, lower alkylamino, and the like.

The term "suitable substituent", "substituent" or "substituted" used in conjunction with the groups described herein refers to a chemically and pharmaceutically acceptable group, i.e., a moiety that does not negate the therapeutic activity of the inventive compounds. It is understood that substituents and substitution patterns on the compounds of the invention may be selected by one of ordinary skill in the art to provide compounds that are chemically stable and that can be readily synthesized by techniques known in the art, as well as those methods set forth below. If a substituent is itself substituted with more than one group, it is understood that these multiple groups may be on the same carbon/member atom or on different carbons/member atoms, as long as a stable structure results. Illustrative examples of some suitable substituents include, cycloalkyl, heterocyclyl, hydroxyalkyl, benzyl, carbonyl, halo, haloalkyl, perfluoroalkyl, perfluoroalkoxy, alkyl, alkenyl, alkynyl, hydroxy, oxo, mercapto, alkylthio, alkoxy, aryl or heteroaryl, aryloxy or heteroaryloxy, aralkyl or heteroaralkyl, aralkoxy or heteroaralkoxy, HO—(C=O)—, amido, amino, alkyl- and dialkylamino, cyano, nitro, carbamoyl, alkylcarbonyl, alkoxycarbonyl, alkylaminocarbonyl, dialkylaminocarbonyl, arylcarbonyl, aryloxycarbonyl, alkylsulfonyl, and arylsulfonyl. Typical substituents include aromatic groups, substituted aromatic groups, hydrocarbon groups including alkyl groups such as methyl groups, substituted hydrocarbon groups such as benzyl, and heterogeneous groups including alkoxy groups such as methoxy groups.

The term "fused" means in which two or more carbons/member atoms are common to two adjoining rings, e.g., the rings are "fused rings".

Cross-linking agent(s) are provided. The cross-linking agent(s) described herein may be used for making composition(s) such as desired polymeric composition(s). In certain embodiments, the cross-linking agent(s) can be used to make hydrogel material(s), which includes, and without being limited thereto, silicon hydrogel materials. Such materials/compositions are useful in the manufacture of biocompatible medical devices, for example, having desirable physical properties for use as contact lense(s) and/or stimulating device(s).

In embodiments, the cross-linking agent(s) described herein possess dual-reactivity.

In additional embodiments, hydrogel material(s) or silicon hydrogel material(s) are prepared from at least one (meth)acrylate monomer, at least one N-vinyl pyrolidone or its derivatives, and one or more cross-linking agent(s)(s). The cross-linking agent(s) described herein possess dual-reactivity. For example, the cross-linking agent(s) can provide at least some crosslinks between the polymer chains that essentially comprise units of (meth)acrylate monomer and the polymer chains that essentially comprise units of vinyl monomer and N-vinyl pyrolidone units. This dual-reactive reactive approach allows a person of ordinary skill to tune the hydrogel matrix in which some hydrophilic vinyl polymer chains or acrylamide chains have a greater ability to move or migrate within the hydrogel polymeric framework than other hydrophilic vinyl polymer chains, particularly in a physiological aqueous environment. Without being bound by theory, the dual-reactive approach of the cross-linking agent(s)(s) is believed to anchor some hydrophilic vinyl polymer chains and acrylamide chains to the (meth)acrylate polymer chain more strongly than others to create a dimensionally stable, hydrogel polymer framework, and other vinyl polymer chains have relatively greater mobility within the same framework. Moreover, these anchored vinyl chains can be further anchored to the hydrogel framework through additional crosslinks within the (meth)acrylate framework. It is this type of molecular anchoring of hydrophilic vinyl polymer that may explain, in embodiments, the observed surface enhancement (wettability and/or lubricity) along with optimal physical properties such as modulus of elasticity, oxygen permeability, and a low level of extractables during manufacture—all of which, collectively, must be considered and balanced for a contact lens that a consumer demands in terms of its comfort over at least 18 hours (in the case of a daily replacement lens), or over two to four weeks (in the case of an extended wear lens). The term, physiological aqueous environment, means an aqueous borate-buffered saline (BBS) solution with a pH of 7.4-7.5, a compositional solution well known to a person of ordinary skill in the art of hydrogel materials for medical devices.

In embodiments, matching the reactivity of each monomer in the polymer composition using the cross-linking agent(s) described herein may provide for a relatively consistent hydrogel polymer framework, which is a commercial consideration in that the hydrogel material can be reproduced within production specifications for a given polymerization monomer mix. Such consistency is useful when it comes to the dimensional stability of the hydrogel matrix over time, e.g., in typical embodiments, a contact lens should maintain dimensional stability in its packaging for at least three years or more as well as maintain dimensional stability when positioned in the eye. Prior copolymerizations of at least one (meth)acrylate monomer with at least one vinyl monomer and a conventional cross-linking agent(s) do not consistently exhibit this level of dimensional stability.

In other embodiments, the cross-linking agent(s) are designed for dual-phase polymerization as they are designed with dual reactive sites in one agent to polymerize and incorporate both the (meth)acrylate (fast) and vinyl (slow), i.e., monomers of two different free-radical polymerization rates, into a hydrogel polymer framework or network. In the absence of such a cross-linking agent(s), the formed interpenetrating poly(NVP) is too mobile within the hydrogel framework, and as the hydrogel swells in a physiological aqueous environment, the poly(NVP) is released from the framework. Moreover, in the absence of a dual-reactive cross-linking agent(s), the resulting hydrogel may release a high level of extractables, e.g., low molecular weight poly(NVP) and oligomers, and one often observes a material with poor dimensional stability.

The cross-linking agent(s) may also provide a unique morphology using the dual phase polymerization where specific bioinspired functional monomers, for example, can be incorporated within the hydrogel polymer framework. Persons of skill in the art of making hydrogel materials generally agree that the dual phase polymerizing results in two separate phases—a methacrylate-based phase and a PVP phase. By polymerizing, for example, a fast polymerizing methacrylate phosphatidylcholine (MPC) and a slow polymerizing vinyl phosphatidylcholine carbonate (VPC), each of the two phases can be enriched with the bioinspired polymers. The slow polymerizing VPC is expected to enrich the lens surface (because of its high mobility) and render a highly biocompatible VPC surface. The fast polymerizing MPC is expected to encase the silicone component with a highly hydrophilic polymer, and enhance the wetting and lubricity of the hydrogel surface because even with a dual-phase polymerization some amount of silicone component will be at or near the surface. The resulting hydrogels materials can possess desirable physical characteristics useful for contact lens materials including a low modulus of elasticity, oxygen permeability, suitable tear strength, a low level of extractables, and inherent wettability or lubricity.

In an embodiment, there is provided a compound of formula I:

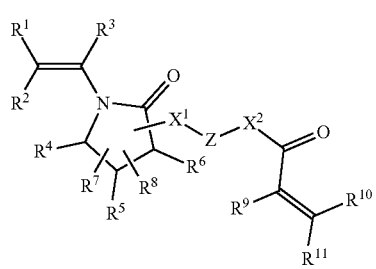

(I)

$R^1$-$R^{11}$ are the same or different, and are each independently selected from H, halo, hydroxyl, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, a substituted or unsubstituted heteroaromatic group, or $NR^aR^b$, wherein $R^a$ and $R^b$ are the same or different, and are independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group;

$X^1$ and $X^2$ are the same or different, and are each independently selected from a direct bond, a heteroatom, C(O), a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, a substituted or unsubstituted heteroaromatic group, or $NR^a$; and Z is selected from a heteroatom, C(O), a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, a substituted or unsubstituted heteroaromatic group, $NR^a$, or $[SiR^{12}R^{13}O]_wSiR^{12}R^{13}$, wherein $R^{12}$ and $R^{13}$ are the same or different, and are independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and w is from 0 to 60.

In another embodiment, there is provided a compound of formula II:

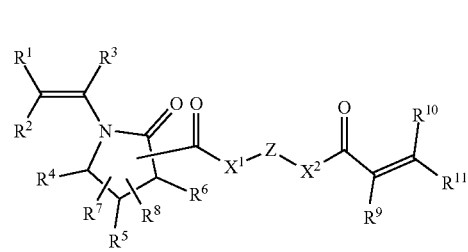

(II)

$R^1$-$R^{11}$ are the same or different, and are each independently selected from H, halo, hydroxyl, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, a substituted or unsubstituted heteroaromatic group, or $NR^aR^b$, wherein $R^a$ and $R^b$ are the same or different, and are independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group;

$X^1$ and $X^2$ are the same or different, and are each independently selected from a direct bond, a heteroatom, C(O), a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, a substituted or unsubstituted heteroaromatic group, or $NR^a$; and Z is selected from a heteroatom, C(O), a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, a substituted or unsubstituted heteroaromatic group, $NR^a$, or $[SiR^{12}R^{13}O]_w SiR^{12}R^{13}$, wherein $R^{12}$ and R are the same or different, and are independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and w is from 0 to 60.

In accordance with further embodiments, $R^1$-$R^{11}$ are the same or different, and are each independently selected from H, halo, hydroxyl, a substituted or unsubstituted hydrocarbon group, or a substituted or unsubstituted heterogeneous group. In other embodiments, $R^1$-$R^{11}$ are the same or different, and are each independently selected from H, halo, hydroxyl, a substituted or unsubstituted $C_1$-$C_6$ alkyl, a substituted or unsubstituted $C_1$-$C_6$ alkoxy, or a substituted or unsubstituted $C_1$-$C_6$ alkanol. In still other embodiments, $R^1$-$R^{11}$ are the same or different, and are each independently selected from H or a substituted or unsubstituted hydrocarbon group. In further embodiments, $R^1$-$R^{11}$ are the same or different, and are each independently selected from H or a substituted or unsubstituted alkyl group. In another embodiment, $R^1$-$R^{11}$ are the same or different, and are each independently selected from H or a substituted or unsubstituted $C_1$-$C_6$ alkyl. In yet another embodiment, $R^1$-$R^{11}$ are the same or different, and are each independently selected from H or unsubstituted $C_1$-$C_6$ alkyl. In another embodiment, $R^1$-$R^{11}$ are the same or different, and are each independently selected from H or methyl. In still other embodiments, $R^1$, $R^2$, $R^{10}$, and $R^{11}$ are H.

In further embodiments, $X^1$ and $X^2$ are the same or different, and are each independently selected from a direct bond, O, $NR^a$, C(O), C(O)$NR^a$, $NR^a$C(O), OC(O)$NR^a$, $NR^a$C(O)O, $NR^a$C(O)NH, NHC(O)$NR^a$, C(O)O, OC(O), NHC(O)NH$Z_0$—NH—C(O)NH, OC(O)NH$Z_0$—NH—C(O)O, OC(O)NH$Z_0$—NH—C(O)NH, or NHC(O)NH$Z_0$—NH—C(O)O; where $Z_0$ is a linear or branched $C_2$-$C_{12}$ alkylene divalent radical, or a $C_5$-$C_7$ cycloaliphatic divalent radical, each of which can optionally include one or more linkages of O, $NR^a$ and C(O). In another embodiment, $X^1$ and $X^2$ are the same or different, and are each independently selected from a direct bond, O, $NR^a$, C(O), C(O)$NR^a$, $NR^a$C(O), $NR^a$C(O), OC(O)$NR^a$, $NR^a$C(O)O, C(O)O, or OC(O). In another embodiment, $R^a$ is selected from H or a substituted or unsubstituted hydrocarbon group. In a further embodiment, $R^a$ is selected from H or unsubstituted $C_1$-$C_6$ alkyl. In an additional embodiment, $R^a$ is selected from H or methyl. In other embodiments, $X^1$ and $X^2$ are the same or different, and are each independently selected from a direct bond, O, or $NR^a$.

In other embodiments, Z is selected from a direct bond, a substituted or unsubstituted hydrocarbon group, a substituted or unsubstituted heterogeneous group, or $[SiR^{12}R^{13}O]_w SiR^{12}R^{13}$. In another embodiment, Z is selected from a direct bond, a substituted or unsubstituted hydrocarbon group, a substituted or unsubstituted heterogeneous group, or $[SiR^{12}R^{13}O]_w SiR^{12}R^{13}$, wherein $R^{12}$ and $R^{13}$ are the same or different, and are independently selected from $C_1$-$C_4$ alkyl or phenyl, and w is from 0 to 60. In yet other embodiments, Z is selected from a direct bond, or a substituted or unsubstituted hydrocarbon group. In other embodiments, Z is selected from a substituted or unsubstituted hydrocarbon group. In certain embodiments, Z is selected from a substituted or unsubstituted alkyl group. In embodiments, Z is selected from a substituted or unsubstituted $C_1$-$C_{20}$ alkyl. In other embodiments, Z is selected from a substituted or unsubstituted $C_1$-$C_6$ alkyl. In further embodiments, Z is selected from an unsubstituted $C_1$-$C_6$ alkyl. In another embodiment, Z is selected from a substituted or unsubstituted aromatic group. In yet other embodiments, Z is selected from a substituted or unsubstituted phenyl group. In other embodiments, Z is selected from a $C_1$-$C_{12}$ unsubstituted or substituted, linear or branched alkylene divalent radical, where each alkylene divalent radical can optionally include one or more linkages of O, $NR^a$, and C(O), an unsubstituted phenylene divalent radical, a $C_5$-$C_7$ cycloaliphatic divalent radical, or a $C_7$-$C_{12}$ arylalkylene divalent radical.

In another embodiment, the compound is Formula III

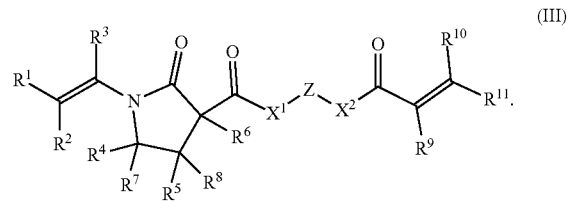

In a further embodiment, the compound is selected from one or more of

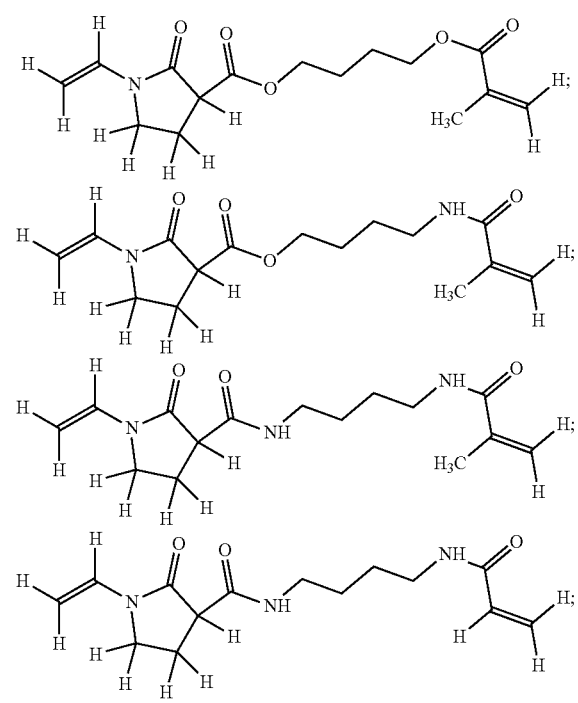

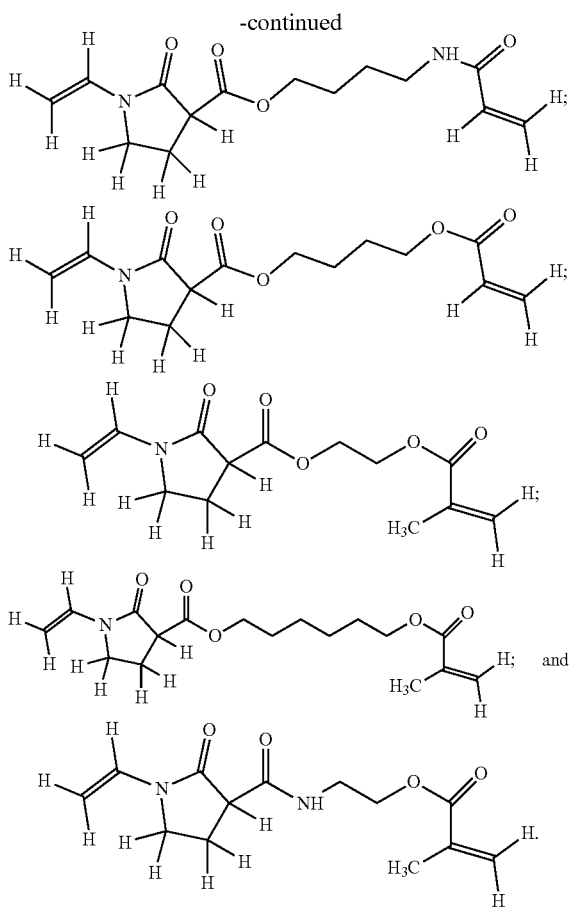

In certain embodiments, the compound is selected from one of the compounds defined above.

In certain embodiments, there is provided a composition comprising one or more of the compounds defined above.

In certain embodiments, the composition comprises one of the compounds defined above.

In further embodiments, the use of one or more of the compounds described above as cross-linking agent(s).

In certain embodiments, the use of one of the compounds described above as cross-linking agent(s).

In other embodiments, the use of one or more of the compounds described above to produce biocompatible medical devices(s).

In certain embodiments, the use of one of the compounds described above to produce biocompatible medical devices(s).

In further embodiments, there is provided a method of producing biocompatible medical devices(s), the method comprising reacting at least one of the compounds described above with at least one monomer.

In other embodiments, there is provides a composition comprising at least one (meth)acrylic monomer, at least one vinyl containing monomer and at least one of the compounds described above. The at least one of the compounds acting as cross-linking agent(s), which include at least one free-radical reactive site for vinyl-containing monomer and at least one free-radical reactive site for meth(acrylic)-containing monomer. Following polymerization by thermal or photochemical initiation, the compositions can provide a hydrogel material with a wettable surface, and in many instances, a surface that is enriched with the slow reacting, poly(cyclic lactam) copolymer component.

Although the above described dual-reactive cross-linking agent(s) and the dual-phase polymerization can be used with many polymeric systems, in particular embodiments, the dual-phase polymerization can be used with hydrogel materials, such as, and without be limiting thereto, both conventional and silicone hydrogels. In addition, the polymer compositions may provide an opportunity to design and plan for an unique morphology using the dual phase polymerization where bioinspired monomers of dual reactivity are simultaneous incorporated with the polymeric network. These hydrogels compositions may possess desirable physical characteristics useful for contact lens materials. Such properties include, for example, low modulus of elasticity, a high level of oxygen permeability, suitable tear strength, a low level of extractables, and inherent wettability or lubricity.

The composition can also include a cross-linking agent(s) that is used to crosslink primarily with the (meth)acrylate monomer in the composition. At times, this second cross-linking agent(s) is referred to herein as a (meth)acrylate cross-linking agent(s). Accordingly, a typical composition may include a dual-reactive cross-linking agent(s) of formulae I, II, or III and a (meth)acrylate cross-linking agent(s).

In embodiments, the cross-linking agent(s) of formulae I, II, or III is present in the composition from 0.02% to 5.0% by weight, from about 0.05% to about 2.0% by weight, or from 0.08% to 0.8% by weight, based on the weight of the total composition excluding the weight of any diluent present in the composition. In fact, all stated percent by weight of any respective component in the described compositions is based on the total weight of the composition excluding the weight of any diluent present in the composition.

In certain embodiments, the compositions include a (meth)acrylate cross-linking agent(s) to provide additional structural stability to the hydrogel polymer framework. Many of these (meth)acrylate cross-linking agent(s) are known in the art of hydrogel materials. The (meth)acrylate cross-linking agent(s) include, but are not limited to, any one difunctional or multifunctional cross-linking agents, and any combination thereof. Representative examples of such cross-linking agents include, but are not limited to, tripropylene glycerol diacrylate, ethylene glycol dimethacrylate, tetraethylene glycol dimethacrylate, poly(ethylene glycol diacrylate) (PEG400 or PEG600), allyl methacrylate and the like. In addition, diacrylates and dimethacrylates of triethylene glycol, butylene glycol, neopentyl glycol, ethylene glycol, hexane-1,6-diol and thio-diethylene glycol; trimethylolpropane triacrylate, N,N'-dihydroxyethylene bisacrylamide, diallyl phthalate, triallyl cyanurate, divinylbenzene, ethylene glycol divinyl ether, or N,N'-methylene-bis-(meth) acrylamide, sulfonated divinylbenzene, divinylsulfone.

If present, the (meth)acrylate cross-linking agent(s) can be used in an effective amount to balance the requirement of a structural hydrogel framework with the water content or the inherent wettability of the resulting hydrogel material. The (meth)acrylate cross link agent can be present in the composition from 0.1% to 3% by weight, from about 0.2% to about 1% by weight, or from 0.2% to 0.6% by weight.

In general embodiments, to achieve a hydrogel material that includes a proper balance of desired properties, particularly, if the hydrogel material is to be a material for a contact lens, the need for a stable hydrogel polymer framework must be balanced with the wettability and lubricity of the hydrogel surface in a physiological aqueous environment. Accordingly, the amount of (meth)acrylate cross link agent may exceed the amount of cross-linking agent(s) of formulae I, II, or III and a hydrogel material with the desired balance of properties can be formed. Accordingly, in one compositional embodiment, the (meth)acrylate cross-linking agent(s) is present in an amount that exceeds the amount of cross link agent of formulae I, II, or III by at least 2×, typically at least 3×, up to about 10×, in terms of percent by weight in the composition. Alternatively, in terms of a weight ratio of (meth)acrylate cross link agent to cross-linking agent(s) of formulae I, II, or III, the weight ratio is from 2:1 to 10:1, typically from 2:1 to 6:1.

The described dual-reactive cross-linking agent(s) are particularly designed for hydrogel formulations that include at least one N-vinyl lactam monomer as the at least one vinyl monomer. Illustrative examples of N-vinyl lactams that are present in the hydrogel formulations, include but not limited to, N-vinyl-2-pyrrolidinone (NVP), N-(1-methyl vinyl) pyrrolidinone, N-vinyl-2-piperidone and N-vinyl-2-caprolactam, each of which can be substituted in the lactam ring by one or more lower alkyl groups such as methyl, ethyl or propyl, e.g., N-vinyl-5-methyl pyrrolidinone, N-vinyl-3,3-dimethyl pyrrolidinone, N-vinyl-5-ethyl pyrrolidinone and N-vinyl-6-methyl piperidone. A typical monomer is N-vinyl-2-pyrrolidinone. Any one of the above N-vinyl lactams can be used alone or in admixture with other lactam monomers to provide hydrogel materials with the properties of interest. Illustrative of the other lactam monomers are, for example, N-vinyl imidazole, N-vinyl succinimide, N-vinyl diglycolylimide, N-vinyl glutarimide, N-vinyl-3-morpholinone and N-vinyl-5-methyl-3-morpholinone.

In a typical hydrogel material, the N-vinyl lactam monomer(s) can be used in conjunction with one or more hydrophobic and/or hydrophilic co-monomers. If used in conjunction with a co-monomer, the N-vinyl lactam will constitute at least 60% of the copolymer and more typically from 70% to 90% by weight of the total monomers present in the monomer formulation.

Furthermore, the ratio of hydrophobic co-monomer to hydrophilic co-monomer present in a monomer formulation in preparing the N-vinyl lactam, can be varied as desired to obtain the particular combination of polymer properties desired for the particular application. The typical amount of N-vinyl lactam in the polymer composition is about 70 to about 90 percent by weight to achieve a relatively high water content of about 70% to about 90% by weight.

Water content is measured by individually placing the lens on a piece of premoistened Whatman #1 filter paper. The surface moisture is removed by lightly smoothing a second piece of premoistened Whatman #1 filter paper over the lens. After checking the accuracy of the balance with two known weights, the lens is placed in a tared weigh boat. The wet weight is recorded to the nearest 0.1 mg and the lens transferred to the lens holder, concave side up (this allows the lens identity to be maintained to match wet and dry weights). After the lens holders are full, they are placed on a spindle with a plastic spacer between them and placed in a glass jar approximately ½ full of desiccant. The jar is capped and the lid tightened, then loosened slightly to prevent pressure buildup. The jar with lenses is placed in a 500-650 watt microwave oven along with a 400 ml beaker containing at least 200 ml of distilled water with boiling beads to keep the jar from becoming overheated. The jar is microwaved at 500-650 watts for 10 minutes; the start time and date are recorded on the paperwork. When the cycle finishes, the jar is removed from the microwave and allowed to cool on the bench for 30 minutes; time out and date are also recorded. When cool, the lenses are individually weighed and their dry weights recorded to the nearest 0.1 mg, matching the dry weights to the corresponding wet weight. The water content is expressed as % water according to the following formula: Water Content is [(wet weight−dry weight)/wet weight]×100.

(Meth)acrylate monomers polymerize very rapidly while the at least one vinyl monomer, polymerizes relatively slowly and fail to effectively copolymerize resulting in a high level of uncrosslinked poly(NVP), the latter of which can be released from the hydrogel resulting in a loss of dimensional stability and a loss of surface wettability. The dual-reactive cross-linking agent(s) described herein can allow one to control the amount of cross-linking of the formed poly(NVP) with the hydrogel network, and in particular the cross linking with the (meth)acrylate polymers of the network. The control of crosslink density can affect the wettability, lubricity, tear strength, extractables and dimensional stability of the resulting hydrogel material. Due to the dual-reactive sites of the described cross-linking agent(s), the agents can form a crosslink between the essentially (meth)acrylate homopolymer and the essentially vinyl homopolymer resulting in hydrogel materials that possess low extractables and excellent dimensional stability.

A hydrogel contact lens prepared with at least 70% by weight of N-vinyl lactam monomer, and a cross-linking agent(s) of formulae I, II, or III, may possess a tear strength of at least about 0.06 N/mm, at least about 0.07 N/mm, or at least about 0.08 N/mm. The hydrogel contact lens may also possess a water content of at least about 40% by weight, at least about 45% by weight, at least about 50% by weight, at least about 65% by weight, at least about 70% by weight, at least about 71% by weight, at least about 77% by weight, or at least about 80% by weight. The hydrogel contact lens may also possess a modulus of elasticity of at least about 0.30 MPa, at least about 0.35 MPa, at least about 0.40 MPa, or at least about 0.45 MPa.

A typical hydrogel contact lens can possess the following mechanical properties: a tear strength of at least about 0.06 N/mm; a water content of at least about 45% by weight; and a modulus of elasticity of at least about 0.30 MPa.

Another typical hydrogel contact lens can possess the following mechanical properties: a tear strength of at least about 0.07 N/mm; a water content of at least about 50% by weight; and a modulus of elasticity of at least about 0.40 MPa.

Another typical hydrogel contact lens can possess the following mechanical properties: a tear strength of at least about 0.08 N/mm; a water content of at least about 65% by weight; and a modulus of elasticity of at least about 0.45 MPa.

The resulting hydrogel materials may possess a highly wettable hydrogel "surface" enriched with the slow reacting monomer/polymer component. The dual reactivity approach can also allow for the surface enrichment, or exposure, of chemical functionality capable of providing for improved clinical performance. This functionality can be bioinspired in nature. For example, the addition of a monomer with vinyl carbonate phosphatidyl choline, which copolymerizes well with NVP, will result in a phosphatidyl choline enriched lens surface. Hydrogel materials with this surface functionality may exhibit such characteristics as a low affinity for proteins, lipids, and bacteria. In addition, the use of bioinspired fast reacting methacrylate based monomer combined with a silicone based monomer can provide for improved wetting and compatibility with the PVP reacting phase.

The chemistry of hydrogels is well known and there exists a variety of monomers that can be used to make the hydrogel materials. In particular, monomers of interest to the contact lens art include, for example, acrylate, acrylamide, methacrylate, methacrylamide, styrene-containing monomers, dimethacrylate and dimethacrylamide monomers, vinyl amide-containing monomers, vinyl carbonate/carbamate/urea monomers, and (meth)acrylate/(meth) acrylamide-capped prepolymers. All of the above-mentioned monomers and prepolymers may further include polysiloxanes and polyfluorosiloxanes, such as ethylenically terminated methacrylate capped urethane-containing polysiloxane prepolymers, fluorine containing polysiloxanes, polyether containing siloxanes, and polysiloxanes monomers, such as, α,ω-bis(methacryloxybutyl) polysiloxane ($M_2 D_{25}$).

Suitable monomers may be represented by the general formulae:

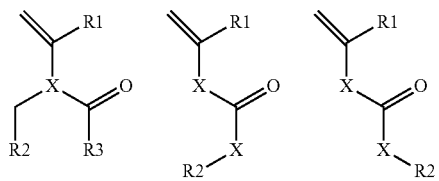

wherein X is O or $NR^c$, where $R^c$ is hydrogen, $C_1$-$C_4$ alkyl or $C_1$-$C_3$ alkanol; R1 is H or $CH_3$; and R2 and R3 are independently hydrogen, a $C_1$-$C_1$ alkyl, $C_3$-$C_{18}$ cycloalkyl, $C_3$-$C_{18}$ cycloalkylalkyl, $C_3$-$C_{18}$ cycloalkenyl, $C_5$-$C_{30}$ aryl, $C_5$-$C_{30}$ arylalkyl, $C_1$-$C_{18}$ alkyl siloxysilane or $C_1$-$C_1$ alkyl siloxane, each of which can be optionally substituted, linear or branched, or R2 and R3 together with the nitrogen atom to which they are bonded are joined together to form a heterocyclic group.

The vinyl monomers of particular interest in hydrogel systems are vinyl hydrophilic monomers, and in particular, a class of N-vinyl hydrophilic monomer. For example, the vinyl hydrophilic monomer is selected from an N-vinylamide monomer of formula A, a vinyl pyrrolidone of formula B, C or D, or an n-vinyl piperidone of formula E:

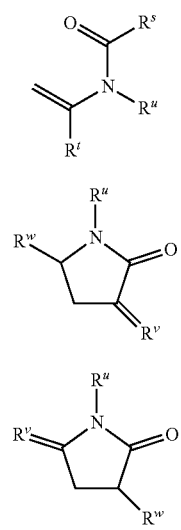

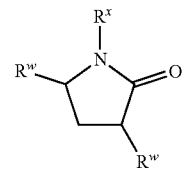

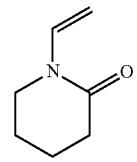

wherein
$R^t$ is H or $CH_3$, and in one embodiment $R^t$ is H;
$R^s$ and $R^w$ are independently selected from H, $CH_3$, $CH_2CH_3$, $CH_2CH_2CH_3$, $C(CH_3)_3$;
$R^u$ is selected from H, $CH_3$, $CH_2CH_3$; and
$R^v$ is selected from $CH_2$, $CHCH_3$ and $C(CH_3)_2$;
$R^x$ is selected from $CH=CH_2$, $CCH_3=CH_2$, and $CH=CHCH_3$.

In one embodiment, the hydrophilic vinyl monomer is selected from ethylene glycol vinyl ether (EGVE), di(ethylene glycol) vinyl ether (DEGVE), and the N-vinyl monomer includes, but not limited to, N-vinyl lactams, including N-vinyl pyrrolidone (NVP), 1-methyl-3-methylene-2-pyrrolidone, 1-methyl-5-methylene-2-pyrrolidone, 5-methyl-3-methylene-2-pyrrolidone; 1-ethyl-5-methylene-2-pyrrolidone, N-methyl-3-methylene-2-pyrrolidone, 5-ethyl-3-methylene-2-pyrrolidone, 1-n-propyl-3-methylene-2-pyrrolidone, 1-n-propyl-5-methylene-2-pyrrolidone, 1-isopropyl-3-methylene-2-pyrrolidone, 1-isopropyl-5-methylene-2-pyrrolidone, N-vinyl-N-methyl acetamide (VMA), N-vinyl-N-ethyl acetamide, N-vinyl-N-ethyl formamide, N-vinyl formamide, N-vinyl acetamide, N-vinyl isopropylamide, allyl alcohol, N-vinyl caprolactam, N-2-hydroxyethyl vinyl carbamate, N-carboxyvinyl-β-alanine (VINAL), N-carboxyvinyl-α-alanine or combinations thereof.

In another embodiment the slow-reacting hydrophilic monomer is selected from NVP, VMA and 1-methyl-5-methylene-2-pyrrolidone, N-vinyl piperidone, N-vinyl-e-caprolactam, N-vinylimidazolidone, N-vinylsuccinimide, N-vinylformamide and N-vinyl urea, N-vinylcarbamate, or combinations thereof. Another vinyl monomer of interest is an O-vinyl carbonate and N-vinyl carbamate that includes zwitterionic functionality such as carboxy betaine and phosphatidyl choline, and mixtures thereof. Because hydrogel materials rich in poly(NVP) have relatively high water content many compositions may include N-vinyl-2-pyrrolidone (NVP), in relatively high concentration, e.g., from 50% to 90% by weight, based on the weight of the total composition excluding the weight of any diluent present in the composition.

The compositions can also include other hydrophilic monomers that are well known in the contact lens art, and include, but not limited to, 2-hydroxyethyl methacrylate (HEMA), glyceryl monomethacrylate (GM) and 2-acrylamido-2-methyl propane sulfonic acid (AMPS). Examples of other hydrophilic monomers useful for polymerization with the vinyl monomer include, but are not limited to, unsaturated carboxylic acids, e.g., acrylic acids, methacrylic acids and the like; (meth)acrylic substituted alcohols, e.g., 3-hydroxypropyl methacrylate, 3-hydroxypropyl acrylate and the like, or combinations thereof. Still other hydrophilic monomers include the azetidinium and the oxazolone-based monomers disclosed in U.S. Pat. No. 4,910,277.

As noted, the additional hydrophilic monomer may be typically (meth)acrylate monomer, and therefore, will typically copolymerize with other (meth)acrylate monomer in the composition with a similar free-radical rate of reactivity. Hydrophilic monomer with hydroxyl functionality is of interest because the hydroxyl functionality can provide additional surface wettability of the resulting hydrogel material. A particular monomer of interest is 2-hydroxyl ethyl methacrylate, which can be present in the composition from 5% to 30% by weight. In a typical composition, the N-vinyl-2-pyrrolidone is present from 30% to 90% by weight, and the 2-hydroxyl ethyl methacrylate is present from 0.5% to 30% by weight.

In the absence of any one silicone-containing monomer, the hydrogels formed are referred to in the art as conventional hydrogels. However, silicone hydrogels is another class of hydrogel materials of importance in the field of medical devices. Accordingly, one or more silicone-containing monomers can be included in a composition of interest. Some well-known silicone-containing monomers include the TRIS-like and trisiloxane (siloxy silane) monomers represented by the following structures.

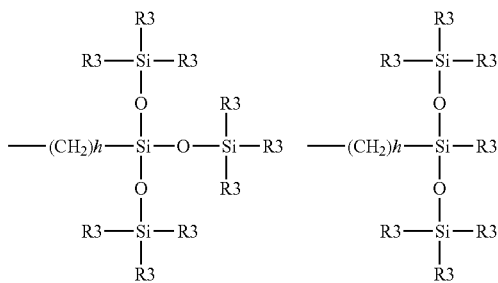

wherein h is 1 to 18 and each $R^3$ independently denotes a lower alkyl radical, or phenyl radical. Representative examples of such acrylate ester and/or methacrylate ester-containing monomers include 3-methacryloyloxypropyltris(trimethylsiloxy)silane or (3-methacryloxy-2-hydroxypropyloxy)propylbis(trimethylsiloxy)-methylsilane), sometimes referred to as TRIS and SIGMA, respectively, and are commercially available from such sources as Gelest, Inc. (Morrisville, PA). Other examples of siloxy silanes include, pentamethyldisiloxanyl methylmethacrylate, phenyltetramethyldisiloxanylethyl acrylate, methyldi(trimethylsiloxy)methacryloxymethyl silane, 3-[tris(trimethylsiloxy)silyl]propyl vinyl carbamate, 3[tris(trimethylsiloxy)silyl] propyol allyl carbamate, 3-tris(trimethylsiloxy)silyl] propyl vinyl carbonate, or combinations thereof. Additional examples of typical siloxy silanes include N-[tris(trimethylsiloxy)silylpropyl]-methacrylamide, N-[tris(dimethylpropyl-siloxy)silylpropyl] methacrylamide, N-[tris(dimethylphenylsiloxy)-silyl propyl](meth)acrylamide, N-[tris(dimethylethylsiloxy)silylpropyl](meth)acrylamide, N-(2-hydroxy-3-(3-(bis(trimethylsilyloxy) methylsilyl)propyloxy)propyl)-2-methyl acrylamide, N-(2-hydroxy-3-(3-(bis(trimethyl-silyloxy)methylsilyl)propyloxy)propyl) acrylamide, N,N-bis[2-hydroxy-3-(3-(bis(trimethylsilyloxy) methylsilyl)propyloxy)propyl]-2-methyl acrylamide, N,N-bis[2-hydroxy-3-(3-(bis(trimethylsilyloxy) methylsilyl)propyloxy)propyl] acrylamide, N-(2-hydroxy-3-(3-(tris(trimethylsilyloxy)silyl)-propyloxy)propyl)-2-methyl acrylamide, N-(2-hydroxy-3-(3-(tris(trimethylsilyloxy)silyl)propyloxy)-propyl)acrylamide, N,N-bis[2-hydroxy-3-(3-(tris(trimethylsilyloxy)silyl)propyloxy)propyl]-2-methyl acrylamide, N,N-bis[2-hydroxy-3-(3-(tris(trimethylsilyloxy)silyl)propyloxy)propyl]acrylamide, N-[2-hydroxy-3-(3-(t-butyldimethylsilyl)propyloxy)propyl]-2-methyl acrylamide, N-[2-hydroxy-3-(3-(t-butyldimethylsilyl)propyloxy)propyl]acrylamide, N,N-bis[2-hydroxy-3-(3-(t-butyldimethylsilyl)-propyloxy)propyl]-2-methyl acrylamide, N,N-bis[2-hydroxy-3-(3-(t-butyldimethylsilyl)propyloxy)-propyl]acrylamide, 3-methacryloxy propylpentamethyl disiloxane, 3-methacryloxy-2-(2-hydroxy ethoxy)-propyloxy)propylbis(trimethylsiloxy) methylsilane, N-2-methacryloxyethyl-O-(methyl-bis-trimethylsiloxy-3-propyl) silyl carbamate, 3-(trimethylsilyl)-propylvinyl carbonate, 3-(vinyloxycarbonylthio)propyl-tris(trimethyl-siloxy)silane, 3-[tris(trimethylsiloxy)silyl]propylvinyl carbamate, 3-[tris(trimethylsiloxy)silyl]propyl allyl carbamate, 3-[tris(trimethylsiloxy)silyl]propyl vinyl carbonate, t-butydimethyl-siloxyethyl vinyl carbonate, trimethylsilylethyl vinyl carbonate, trimethylsilylmethyl vinyl carbonate, or combinations thereof.

Silicone monomers referred in the art as silicone monofunctional monomer can also be included in the described compostions. See, U.S. Pat. No. 8,937,110 to Vanderlaan. Examples of some silicone monofunctional monomer include monomethacryloxyalkyl-polydimethylsiloxane methacrylates selected from monomethacryloxypropyl terminated mono-n-butyl terminated polydimethylsiloxane, monomethacryloxypropyl terminated mono-n-methyl terminated polydimethylsiloxane, monomethacryloxypropyl terminated mono-n-butyl terminated polydiethylsiloxane, monomethacryloxypropyl terminated mono-n-methyl terminated polydiethylsiloxane, N-(2,3-dihydroxypropane)-N'-(propyl tetra(dimethylsiloxy)dimethylbutylsilane) acrylamide, α-(2-hydroxy-1-methacryloxypropyloxypropyl)-o-butyl-decamethyl-pentasiloxane, or combinations thereof.

In another embodiment, the silicone monofunctional monomer is selected from monomethacryloxypropyl terminated mono-n-butyl terminated polydimethylsiloxane, monomethacryloxypropyl terminated mono-n-methyl terminated polydimethylsiloxane, N-(2,3-dihydroxypropane)-N'-(propyl tetra(dimethylsiloxy)dimethylbutylsilane)acrylamide, α-(2-hydroxy-1-methacryloxypropyloxypropyl)-o-butyl-decamethyl-pentasiloxane, or combinations thereof.

In another embodiment the silicone monofunctional monomer is selected from acrylamide silicones general formulae (s1) through (s6) below.

The at least one silicone-containing monomer is present in the described compositions in an amount sufficient to provide the desired oxygen permeability. In certain embodiments, oxygen permeabilities can be greater than about 60 barrers, greater than about 80 barrer, or in some other embodiments greater than about 90 barrer. Suitable amounts will depend on the length of the siloxane chain included in the silicone-containing monomers, with silicone-containing monomers having longer chains requiring less monomer. Amounts include from about 20% to about 60% by weight, and in some embodiments from about 30% to about 55% by weight.

In certain silicone hydrogel compositions, one or more of the silicone-containing monomer above are present in a composition from about 25% to about 80% by weight, or from about 20% to about 80% by weight. In a typical composition, the N-vinyl-2-pyrrolidone is present from about 50% to about 90% by weight, 2-hydroxyl ethyl methacrylate is present from about 0.5% to about 25% by weight, and the silicone-containing monomer is present from about 30% to about 70% by weight.

Specific bioinspired monomers include, but not limited to, carboxybetaines, sulfobetains and phosphobetaines, such as methacryloxy phosphatidyl choline (MPC), N-vinylcarboxy ethyl phosphatidyl choline, O-vinyl ethyl phosphatidyl choline carbonate, 1-(3-sulfopropyl)-2-vinylpyridinium betaine, 3-dimethyl(acryloyloxyethyl) ammonium propyl sulfonate, functional sugars and proteins, or any one mixture of bio-inspired monomer. Other suitable bioinspired hydrophilic monomers will be apparent to one skilled in the art. The bioinspired monomer is present from about 0.5% to about 16% by weight or from about 2% to about 6% by weight.

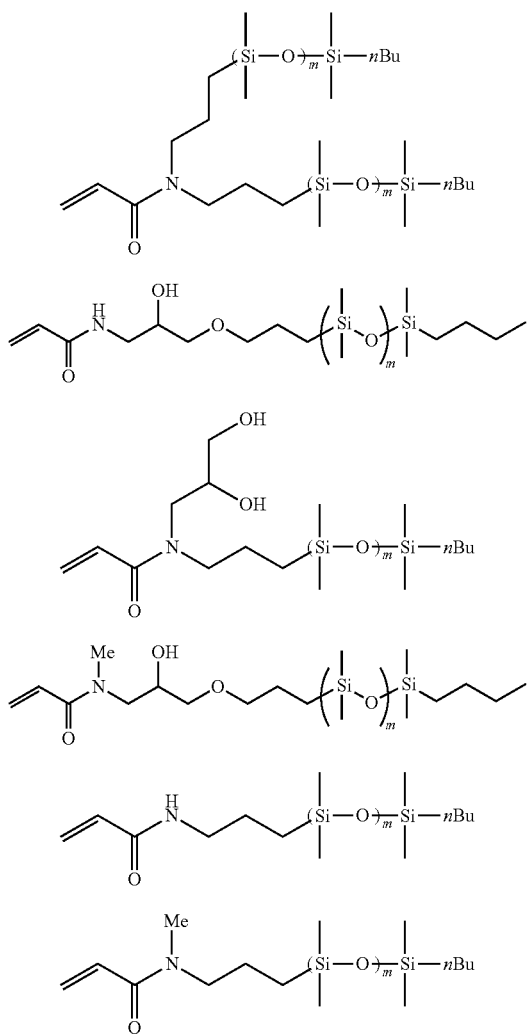

Useful hydrophobic monomers for use herein include, but are not limited to, alkyl acrylates and methacrylates, 4-t-butyl-2-hydroxy cyclohexyl methacrylate (TBE), tert-butyl cyclohexyl methacrylate, isopropylcyclopentyl acrylate, tert-butylcyclohexyl acrylate, isobornyl methacrylate and the like; 2-ethylhexyl methacrylate, 2-phenyloxyethyl meth- acrylate, partially fluorinated acrylates, partially fluorinated methacrylates and the like, or combinations thereof.

In general, the copolymerization reaction can be conducted neat or with a suitable cosolvent. The monomeric mixture and optional cross linking agent(s) are combined in the desired ratio, and then exposed to, for example, ultraviolet (UV) light or electron beams in the presence of one or more photoinitiator(s) or at a suitable temperature, for a time period sufficient to form the copolymer. Heat may also be employed to initiate the polymerization in which case a series of Vazo, peroxide or peroxy initiators, well-known in the art, may be used. Suitable reaction times will ordinarily range from about 1 minute to about 24 hours and typically from about 1 hour to about 10 hours.

The use of UV or visible light in combination with photoinitiators is well known in the art and is particularly suitable for formation of the copolymer. Numerous photoinitiators of the type in question here are commercial products. Photo initiators enhance the rapidity of the curing process when the photo curable compositions as a whole are exposed to, for example, ultraviolet radiation. Suitable photo initiators which are useful for polymerizing the polymerizable mixture of monomers can be commercially available photo initiators. They are generally compounds which are capable of initiating the radical reaction of olefinically unsaturated double bonds on exposure to light with a wavelength of, for example, about 260 to about 480 nm.

Examples of suitable photoinitiators for use herein include, but are not limited to, one or more photoinitiators commercially available under the "IRGACURE", "DAROCUR" and "SPEEDCURE" trade names (manufactures by Ciba Specialty Chemicals, also obtainable under a different name from BASF, Fratelli Lamberti and Kawaguchi), e.g., "IRGACURE" 184 (1-hydroxycyclohexyl phenyl ketone), 907 (2-methyl-1-[4-(methylthio)phenyl]-2-morpholino propan-1-one), 369 (2-benzyl-2-N,N-dimethylamino-1-(4-morpholinophenyl)-1-butanone), 500 (the combination of 1-hydroxy cyclohexyl phenyl ketone and benzophenone), 651 (2,2-dimethoxy-2-phenyl acetophenone), 1700 (the combination of bis(2,6-dimethoxybenzoyl-2,4,4-trimethyl pentyl) phosphine oxide and 2-hydroxy-2-methyl-1-phenyl-propan-1-one), and 819 [bis(2,4,6-trimethyl benzoyl)phenyl phosphine oxide] and "DAROCUR" 1173 (2-hydroxy-2-methyl-1-phenyl-1-propan-1-one) and 4265 (the combination of 2,4,6-trimethylbenzoyldiphenyl-phosphine oxide and 2-hydroxy-2-methyl-1-phenyl-propan-1-one); and the like and mixtures thereof. Other suitable photo initiators for use herein include, but are not limited to, diphenyl(2,4,6-trimethylbenzoyl)phosphine oxide (TPO) and ethyl (2,4,6-trimethylbenzoyl) phenylphosphinate (TPO-L), alkyl pyruvates such as methyl, ethyl, propyl, and butyl pyruvates, and aryl pyruvates such as phenyl, benzyl, and appropriately substituted derivatives thereof. Generally, the amount of photo initiator can range from about 0.05% w/w to about 5% w/w and typically from about 0.1% w/w to about 1% w/w.

Examples of suitable thermal initiators for use herein include, but are not limited to, include the azo and peroxy type compounds, such as 2,2-azobisisobutyronitrile (VAZO 64) (AIBN), 4,4-azobis(4-cyanovaleric acid), 1,1-azobis(cyclohexanecarbonitrile), benzoyl peroxide, 1,1-bis(tert-butylperoxy)cyclohexane, tert-butyl hydroperoxide, tert-butyl peroxybenzoate and dicumyl peroxide. Generally, the amount of thermal initiator can range from about 0.05% w/w to about 5% w/w and typically from about 0.1% w/w to about 1% w/w.

An organic diluent (solvent) can be included in any one composition of interest. As used herein, the term "organic diluent" encompasses organic compounds which minimize incompatibility of the components in the initial monomeric mixture and are substantially nonreactive with the components in the initial mixture. Additionally, the organic diluent serves to minimize phase separation of polymerized products produced by polymerization of the monomeric mixture. Also, the organic diluent will generally be relatively nonflammable. Contemplated organic diluents include alcohols such as tert-butanol (TBA), tert-amyl alcohol, diols, such as ethylene glycol; and polyols, such as glycerol. Typically, the organic diluent is water soluble and can be removed easily through a water extraction process. Other suitable organic diluents would be apparent to a person of ordinary skill in the art.

The organic diluent is included in an amount effective to provide the desired effect (for example, minimal phase separation of polymerized products). Generally, the diluent is included at 0 to 60% by weight of the monomeric mixture, with about 1% to about 40% by weight being more typical, about 2% to about 30% by weight being even more typical and about 3% to about 25% by weight being especially typical.

The compositions described can also include at least one UV absorbing compound. Surprisingly, UV absorbing compounds can have a substantially different impact on the reaction kinetics of the reactive components in the reaction mixtures of the present invention. For example, it has been found that benzotriazoles substantially slow the rate of reaction for NVP and TEGDMA is some systems much more than the reaction rates of the silicone-containing components. In the case of NVP, this can be beneficial, as it can provide additional processing flexibility and an exceptional balance of properties, including water contents in excess of about 60%, haze values less than about 50%, or less than about 10%, advancing contact angles less than about 60° and Dk's greater than about 80.

When the silicone hydrogel is used as an ophthalmic device it may be desirable to incorporate a reactive UV absorbing compound in the reaction mixture so that the resulting silicone hydrogel will be UV absorbing. However, in another embodiment nonreactive UV absorbing compounds may be used solely to achieve the desired reaction kinetics. Alternatively, solution filters may be used. It is believed that the UV absorbers in the reactive mixtures block incident light below about 370 nm which alters the spectrum of light being imposed on the visible photoinitiator. This tends to reduce the rate of initiation as well as lower the concentration of initiator radicals present, which in turn is believed to have a significant impact on the rate of polymerization of the monomers. Typically, the monomers which are likely to be most significantly impacted are the slowest and fastest. In several of the examples included herein, NVP (slowest) and TEGDMA (the fastest) are the most sensitive to the presence of the UV absorber.

Suitable UV absorbers may be derived from 2-(2'-hydroxyphenyl)benzotriazoles, 2-hydroxybenzophenones, 2-hydroxyphenyltriazines, oxanilides, cyanoacrylates, salicylates and 4-hydroxybenzoates; which may be further reacted to incorporate reactive polymerizable groups, such as (meth)acrylates. Specific examples of UV absorbers which include polymerizable groups include 2-(2'-hydroxy-5-methacrylyloxyethylphenyl)-2H-benzotriazole (Norbloc), 5-vinyl and 5-isopropenyl derivatives of 2-(2,4-dihydroxyphenyl)-2H-benzotriazole and 4-acrylates or 4-methacrylates of 2-(2,4-dihydroxyphenyl)-2H-benzotriazole or 2-(2, 4-dihydroxyphenyl)-1,3-2H-dibenzotriazole, mixtures thereof and the like. When a UV absorber is included, it may be included in amounts between about 0.5% and about 4% by weight, and suitably between about 1% and about 2% by weight.

The present invention relates to monomeric formulations useful in the manufacture of biocompatible medical devices. More particularly, the present invention relates to hydrogel formulations capable of polymerization to form polymeric compositions having desirable physical properties useful in the manufacture of contact lenses. Such properties may include low modulus of elasticity, a high level of oxygen permeability, wettability, lubricity and a low level of extractables.

According to the present process, the non-silicone and silicon containing monomeric mixture, comprising at least one hydrophilic monomer, and an optionally the organic diluent, is shaped and cured by conventional methods such as static casting or spincasting. The cross-linking agent(s) is useful for a wide variety of polymeric materials, either rigid or soft. Especially typical polymeric materials are lenses including contact lenses, phakic and aphakic intraocular lenses and corneal implants although all polymeric materials including biomaterials are contemplated as being within the scope of this invention. Typical articles are optically clear and useful as a contact lens.

The cross-linking agent(s) can be prepared by a variety of synthetic routes. Moreover, many of the cross-linking agent(s) can be stable and non-volatile under common polymerization conditions used in the art. In one embodiment, the reaction of 1-vinylpyrrolidin-2-one-3-carboxylic acid with hydroxyethylmethacrylate (HEMA) will result in cross-linking agent (1). See, Scheme 1.

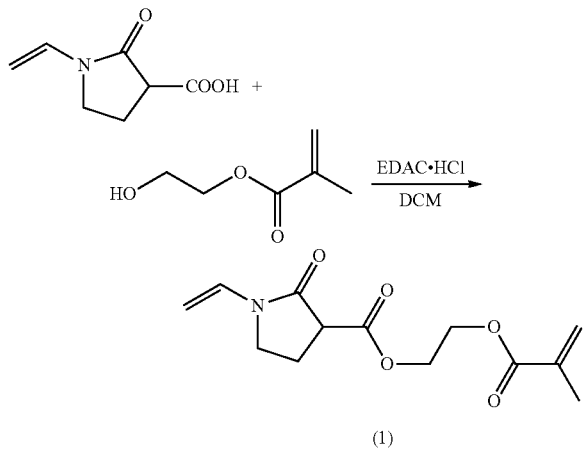

In another embodiment, the reaction of 1-vinylpyrrolidin-2-one with oxirane or an alkyl halide, followed by a reaction with an acyl chloride will result in cross-linking agent (4). See, Scheme 2.

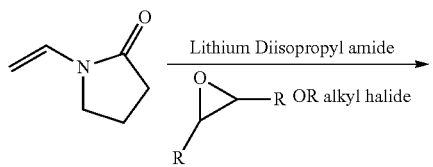

-continued

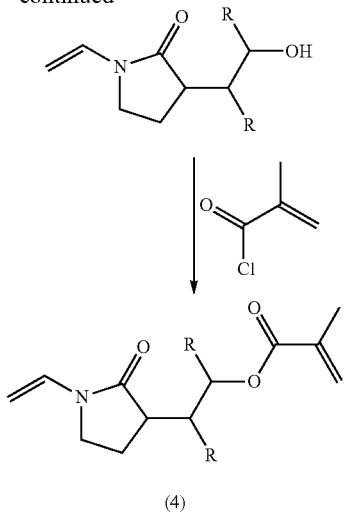

(4)

Other embodiments are shown in the examples below. In general, and without being limited thereto, synthesis can include reacting a carbanion of the N-vinylpyrrolidin-2-one (e.g. nucleophile) with an electrophile (e.g. oxirane or alkyl halide) followed by esterification; reacting an N-vinylpyrrolidin-2-one having a leaving group (on a ring carbon) with a nucleophile (e.g. amine/amide or alcohol); or reacting a carboxylic acid substituted N-vinylpyrrolidin-2-one-3-carboxylic acid with an alcohol or amide. One skilled in the art would understand the various substituted substrates that may be used.

Lens formation can be by free radical polymerization such as azobisisobutyronitrile (AIBN) and peroxide catalysts using initiators and under conditions such as those set forth in U.S. Pat. No. 3,808,179, incorporated herein by reference. Photoinitiation of polymerization of the monomer mixture as is well known in the art may also be used in the process of forming an article as disclosed herein. Following hydration, the shaped article, for example a lens for custom optics lens, is optionally machined by various processes known in the art. The machining step includes lathe cutting a lens surface, lathe cutting a lens edge, buffing a lens edge or polishing a lens edge or surface. The present process is particularly advantageous for processes wherein a lens surface is lathe cut, since machining of a lens surface is especially difficult when the surface is tacky or rubbery. The described hydrogel materials can also be prepared by film casting.

The examples should not be read as limiting the scope of the invention as defined in the claims. Unless clearly stated otherwise all numerical percentages, e.g., percentage amounts of monomer in a polymerization mixture, are listed as weight percent, supra.

The compositions described herein can be used to make hydrogel materials for a biomedical device such as artificial heart valves, films, surgical devices, vessel substitutes, intrauterine devices, membranes, diaphragms, surgical implants, artificial blood vessels, artificial ureters, artificial breast tissue and membranes intended to come into contact with body fluid outside of the body, e.g., membranes for kidney dialysis and heart/lung machines and the like, catheters, mouth guards, denture liners, ophthalmic devices, and especially hydrogel contact lenses.

As used herein, a "biomedical device" is any article that is designed to be used while either in or on mammalian tissues or fluid, and in one embodiment in or on human tissue or fluids. Examples of these devices include but are not limited to catheters, implants, stents, and ophthalmic devices such as intraocular lenses, punctal plugs and contact lenses.

The transitional term "comprising", which is synonymous with "including," "containing," or "characterized by," is inclusive or open-ended and does not exclude additional, unrecited elements or method steps. The transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

For the purposes of this specification and appended claims, unless otherwise indicated, all numbers expressing quantities, percentages or proportions, and other numerical values used in the specification and claims, are to be understood as being modified in all instances by the term "about." Furthermore, all ranges disclosed herein are inclusive of the endpoints and are independently combinable. Whenever a numerical range with a lower limit and an upper limit are disclosed, any number falling within the range is also specifically disclosed.

Any term, abbreviation or shorthand not defined is understood to have the ordinary meaning used by a person skilled in the art at the time the application is filed. The singular forms "a," "an," and "the," include plural references unless expressly and unequivocally limited to one instance.

EXAMPLES

All monomer components (both silicone and hydrophilic monomers) were purified before use. Mechanical properties were determined on samples stored in BBS using ASTM Instron methods. Oxygen permeability values were measured using the polarographic probe method. Films were prepared via polymerization between treated glass plates having a suitable inert spacer. The films were extracted in distilled water and/or in 2-propanol, hydrated in borate-buffered saline (pH 7.3) and autoclaved for 30 minutes. Wetting angle was performed via the captive bubble techniques. All of the above methods and analytical techniques are well known to a person of ordinary skill in the art.

Example 1: Synthesis of Cross-Linking Agent (1)

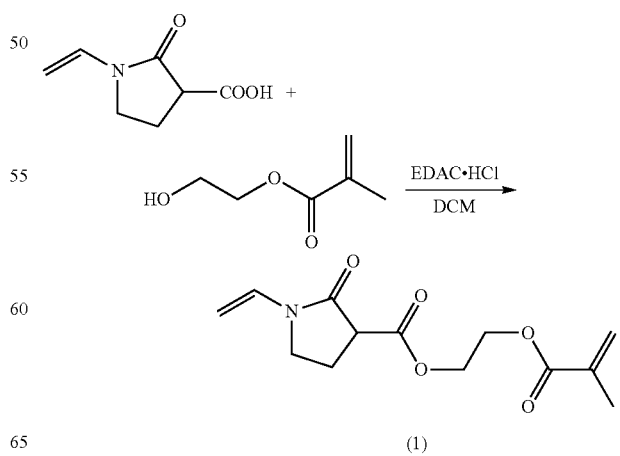

(1)

In a dry 250 mL round bottom flask was added the 1-vinylpyrrolidin-2-one-3-carboxylic acid (1.6 g, 10.3 mmol), diluted in 40 mL of dichloromethane (DCM), and then hydroxyethylmethacrylate (HEMA) (1.4 g, 10.7 mmol, 1.05 eq.) was added and the solution was stirred for 15 minutes. 1-(3-Dimethylaminopropyl)-3-ethylcarbodiimide hydrochloride (EDAC·HCl) (2.35 g, 12.2 mmol, 1.2 eq.) was then added and the solution was stirred for 1 h at room temperature and monitored by HPLC. Water (25 mL) was then added to the solution and the organic layer was separated. The organic layer was then washed with water (3×25 mL), and then dried with Na$_2$SO$_4$, filtered, and solvent was evaporated to give a crude product as yellow oil. The yellow oil was then purified by column chromatography (0 to 10% DCM/EtOAc) to afford the crosslinker as a colorless oil (78%). The HPLC purity was determined at 97% and the NMR spectrum conforms to the structure (1): $^1$H-NMR (CDCl$_3$): 7.05 (1H, dd, J=9, 16 Hz), 6.15 (1H, s), 5.62-5.59 (1H, m), 4.56-4.37 (6H, m), 3.70-3.63 (1H, m), 3.59 (1H, dd, J=7, 10 Hz), 3.55-3.48 (1H, m), 2.55-2.45 (1H, m), 2.43-2.33 (1H, m).

Example 1A: Synthesis of Cross-Linking Agent (2)

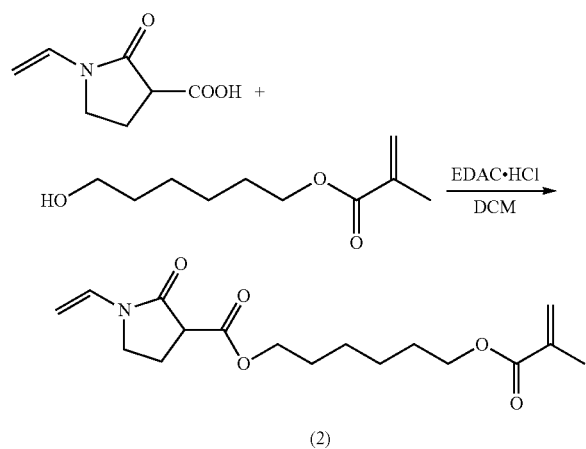

(2)

In a dry 250 mL round bottom flask was added the 1-vinylpyrrolidin-2-one-3-carboxylic acid (1 g, 6.44 mmol), diluted in 40 mL of dichloromethane (DCM), and then 6-hydroxyhexyl methacrylate (1.21 g, 6.44 mmol, 1.0 eq.) was added and the solution was stirred for 15 minutes. 1-(3-Dimethylaminopropyl)-3-ethylcarbodiimide hydrochloride (EDAC·HCl) (1.39 g, 7.25 mmol, 1.12 eq.) was then added and the solution was stirred for 1 h at room temperature and monitored by HPLC. Water (40 mL) was then added to the solution and the organic layer was separated. The organic layer was then washed with water (3×40 mL), and then dried with Na$_2$SO$_4$, filtered, and solvent was evaporated to give a crude product as yellow solid. The yellow solid was then purified by column chromatography to afford the crosslinker as off white solid (71%). The HPLC purity was determined at 97% and the NMR spectrum conforms to the structure (2): $^1$H-NMR (CDCl$_3$): 6.9 (1H, dd), 6.4 (1H, s), 6.48 (1H, s) 5.8 (1H, s), 4.2 (1H, s), 4.1 (2H, t), 3.9 (2H, t), 3.5-3.6 (4H, m), 3.06 (1H, s), 2.1 (3H, s), 1.62-1.43 (8H, m)

Example 1B: Synthesis of Cross-Linking Agent (3)

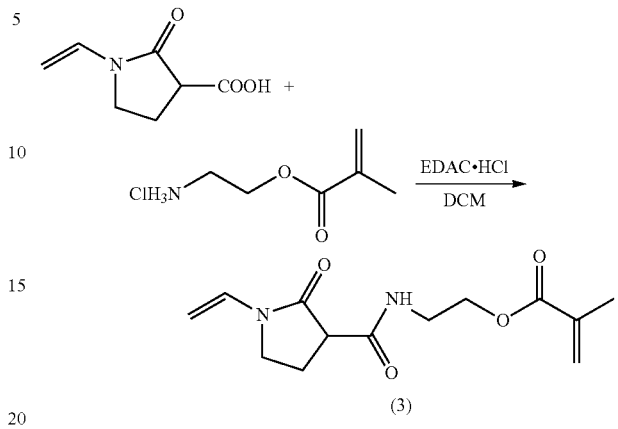

(3)

In a dry 250 mL round bottom flask was added the 1-vinylpyrrolidin-2-one-3-carboxylic acid (1 g, 6.44 mmol), diluted in 40 mL of dichloromethane (DCM), and then 2-aminoethyl methacrylate (1.07 g, 6.44 mmol, 1.0 eq.) was added and the solution was stirred for 15 minutes. 1-(3-Dimethylaminopropyl)-3-ethylcarbodiimide hydrochloride (EDAC·HCl) (1.39 g, 7.25 mmol, 1.12 eq.) was then added and the solution was stirred for 1 h at room temperature and monitored by HPLC. Water (80 mL) was then added to the solution and the organic layer was separated. The organic layer was then washed with water (3×70 mL), and then dried with Na$_2$SO$_4$, filtered, and solvent was evaporated to give a crude product as yellow solid. The yellow solid was then purified by column chromatography to afford the crosslinker as off white solid (56%). The HPLC purity was determined at 96% and the NMR spectrum conforms to the structure (3): $^1$H-NMR (CDCl$_3$): 8.03 (1H, s), 6.96 (1H, dd), 6.4 (1H, s), 6.48 (1H, s) 5.78 (1H, m), 5.7-4.6 (1H, m), 4.3 (2H, t), 4.1 (2H, t), 3.6-3.5 (4H, m), 3.06 (1H, s), 1.98 (3H, s)

Example 2. Hydrogel Contact Lenses

Examples 2A and 2B

Hydrogel contact lenses were prepared from each formulation examples 2A and 2B. The contact lenses were prepared from a monomer formulation that includes hydroxyethylmethacrylate (HEMA), 1-Vinyl-2-pyrrolidinone (NVP), ethylene glycol dimethacrylate (EGDMA), cross-linking agent (1) and diphenyl(2,4,6-trimethylbenzoyl)phosphine oxide (TPO). The amounts of the monomers and cross-linking agent (1) are shown in Table 1:

TABLE 1

| | 2A (wt %) | 2B (wt %) |
| --- | --- | --- |
| HEMA | 79.5 | 45 |
| NVP | 19.0 | 53.5 |
| EGDMA | 0.5 | 0.5 |
| CROSS-LINKING AGENT (1) | 0.5 | 0.5 |
| TPO | 0.5 | 0.5 |

The monomer formulation mixture was mixed well using magnetic stirrer and then degassed for 10 minutes using dry nitrogen stream. The mixed formulation was added to unpurged polypropylene lens molds, and the filled molds were placed in an UV chamber for 15 minutes.

The lenses were removed from the UV-chamber and allowed to cool to room temperature. The lenses were dry released from the molds. Alternatively, the lenses can be wet released from the mold. Dry release or wet release methods are well known to those of ordinary skill in the contact lens art.

Examples 2C and 2D

Hydrogel contact lenses were prepared from each formulation examples 2C and 2D. The contact lenses were prepared from a monomer formulation that includes glycidyl methacrylate (GMMA), 1-Vinyl-2-pyrrolidinone (NVP), ethylene glycol dimethacrylate (EGDMA), cross-linking agent (1) and diphenyl(2,4,6-trimethylbenzoyl)phosphine oxide (TPO). The amounts of the monomers and cross-linking agent (1) are shown in Table 2:

TABLE 2

|  | 2C (wt %) | 2D (wt %) |
| --- | --- | --- |
| GMMA | 79.5 | 45 |
| NVP | 19.0 | 53.5 |
| EGDMA | 0.5 | 0.5 |
| CROSS-LINKING AGENT (1) | 0.5 | 0.5 |
| TPO | 0.5 | 0.5 |

The monomer formulation mixture was mixed well using magnetic stirrer and then degassed for 10 minutes using dry nitrogen stream. The mixed formulation was added to unpurged polypropylene lens molds, and the filled molds were placed in an UV chamber for 15 minutes.

The lenses were removed from the UV-chamber and allowed to cool to room temperature. The lenses were dry released from the molds. Alternatively, the lenses can be wet released from the mold. Dry release or wet release methods are well known to those of ordinary skill in the contact lens art.

Example 2E and 2F

Hydrogel contact lenses were prepared from each formulation examples 2E and 2F. The contact lenses were prepared from a monomer formulation that includes dimethylacrylamide (DMA), 1-Vinyl-2-pyrrolidinone (NVP), ethylene glycol dimethacrylate (EGDMA), cross-linking agent (1) and diphenyl(2,4,6-trimethylbenzoyl)phosphine oxide (TPO). The amounts of the monomers and cross-linking agent (1) are shown in Table 3:

TABLE 3

|  | 2E (wt %) | 2F (wt %) |
| --- | --- | --- |
| DMA | 79.5 | 45 |
| NVP | 19.0 | 53.5 |
| EGDMA | 0.5 | 0.5 |
| CROSS-LINKING AGENT (1) | 0.5 | 0.5 |
| TPO | 0.5 | 0.5 |

The monomer formulation mixture was mixed well using magnetic stirrer and then degassed for 10 minutes using dry nitrogen stream. The mixed formulation was added to unpurged polypropylene lens molds, and the filled molds were placed in an UV chamber for 15 minutes.

The lenses were removed from the UV-chamber and allowed to cool to room temperature. The lenses were dry released from the molds. Alternatively, the lenses can be wet released from the mold. Dry release or wet release methods are well known to those of ordinary skill in the contact lens art.

Examples 2G and 2H

Hydrogel contact lenses were prepared from formulation examples 2G and 2H. The contact lenses were prepared from a monomer formulation that includes 3-(tris-(trimethylsiloxy)silyl)propyl methacrylate (TRIS), 1-Vinyl-2-pyrrolidinone (NVP), ethylene glycol dimethacrylate (EGDMA), cross-linking agent (1) and diphenyl(2,4,6-trimethylbenzoyl)phosphine oxide (TPO). The amounts of the monomers and cross-linking agent (1) are shown in Table 4:

TABLE 4

|  | 2G (wt %) | 2H (wt %) |
| --- | --- | --- |
| TRIS | 79.5 | 45 |
| NVP | 19.0 | 53.5 |
| EGDMA | 0.5 | 0.5 |
| CROSS-LINKING AGENT (1) | 0.5 | 0.5 |
| TPO | 0.5 | 0.5 |

The monomer formulation mixture was mixed well using magnetic stirrer and then degassed for 10 minutes using dry nitrogen stream. The mixed formulation was added to unpurged polypropylene lens molds, and the filled molds were placed in an UV chamber for 15 minutes.

The lenses were removed from the UV-chamber and allowed to cool to room temperature. The lenses were dry released from the molds. Alternatively, the lenses can be wet released from the mold. Dry release or wet release methods are well known to those of ordinary skill in the contact lens art.

Examples 2I and 2J

Hydrogel contact lenses were prepared from formulation examples 2I and 2J. The contact lenses were prepared from a monomer formulation that includes 3-methacryloxy-2-hydroxypropyloxy)propylbis(trimethylsiloxy)-methylsilane (SIGMA), 1-Vinyl-2-pyrrolidinone (NVP), ethylene glycol dimethacrylate (EGDMA), cross-linking agent (1) and diphenyl(2,4,6-trimethylbenzoyl)phosphine oxide (TPO). The amounts of the monomers and cross-linking agent (1) are shown in Table 5:

TABLE 5

|  | 2I (wt %) | 2J (wt %) |
| --- | --- | --- |
| SIGMA | 79.5 | 45 |
| NVP | 19.0 | 53.5 |
| EGDMA | 0.5 | 0.5 |
| CROSS-LINKING AGENT (1) | 0.5 | 0.5 |
| TPO | 0.5 | 0.5 |

The monomer formulation mixture was mixed well using magnetic stirrer and then degassed for 10 minutes using dry nitrogen stream. The mixed formulation was added to unpurged polypropylene lens molds, and the filled molds were placed in an UV chamber for 15 minutes.

The lenses were removed from the UV-chamber and allowed to cool to room temperature. The lenses were dry released from the molds. Alternatively, the lenses can be wet released from the mold. Dry release or wet release methods are well known to those of ordinary skill in the contact lens art.

TABLE 6

Mechanical Properties of Examples 2A to 2F and 2H

| Property | 2A | 2B | 2C | 2D | 2E | 2F | 2H |
|---|---|---|---|---|---|---|---|
| % Ext. 0.9 Saline | 5 | 8 | 6.7 | 9 | 6.5 | 10 | 5 |
| Modulus MPa | 0.33 | 0.42 | 0.41 | 0.50 | 0.39 | 0.45 | 0.45 |
| Tear N/mm | 0.08 | 0.07 | | | | | 0.08 |
| Water Content (IPA Ext. Only) | 50.3 | 68 | 45 | 70 | 57 | 71 | 48.3 |
| Contact Angle | 44 | 41 | 40 | — | 44 | — | 37 |
| Hardness | — | — | — | — | — | — | — |

Examples 2K and 2L

Hydrogel contact lenses were prepared from each formulation examples 2K and 2L. The contact lenses were prepared from a monomer formulation that includes hydroxyethylmethacrylate (HEMA), 1-Vinyl-2-pyrrolidinone (NVP), poly(ethylene glycol) diacrylate) (pEGDA), cross-linking agent (1) and diphenyl(2,4,6-trimethylbenzoyl)phosphine oxide (TPO). The amounts of the monomers and cross-linking agent (1) are shown in Table 7:

TABLE 7

| | 2K (wt %) | 2L (wt %) |
|---|---|---|
| HEMA | 79.5 | 45 |
| NVP | 19.0 | 53.5 |
| pEGDA | 0.5 | 0.5 |
| CROSS-LINKING AGENT (1) | 0.5 | 0.5 |
| TPO | 0.5 | 0.5 |

The monomer formulation mixture was mixed well using magnetic stirrer and then degassed for 10 minutes using dry nitrogen stream. The mixed formulation was added to unpurged polypropylene lens molds, and the filled molds were placed in an UV chamber for 15 minutes.

The lenses were removed from the UV-chamber and allowed to cool to room temperature. The lenses were dry released from the molds. Alternatively, the lenses can be wet released from the mold. Dry release or wet release methods are well known to those of ordinary skill in the contact lens art.

Example 2M, 2N, 2O, 2P

Hydrogel contact lenses were prepared from formulation examples 2M, 2N, 2O and 2P. The contact lenses were prepared from a monomer formulation that includes hydroxyethylmethacrylate, 1-Vinyl-2-pyrrolidinone (NVP), ethylene glycol dimethacrylate (EGDMA), cross-linking agent (1) and ethyl (2,4,6-trimethylbenzoyl) phenylphosphinate (TPO-L). The amounts of the monomers and cross-linking agent (1) are shown in Table 8:

TABLE 8

| | 2M (wt %) | 2N (wt %) | 2O (wt %) | 2P (wt %) |
|---|---|---|---|---|
| HEMA | 68.45 | 58.45 | 57.65 | 57.95 |
| NVP | 30 | 40 | 40 | 40 |
| EGDMA | 0.5 | 0.5 | 0.9 | 0.9 |
| CROSS-LINKING AGENT (1) | 0.5 | 0.5 | 0.9 | 0.6 |
| TPO-L | 0.5 | 0.55 | 0.55 | 0.55 |

The monomer formulation mixture was mixed well using magnetic stirrer and then degassed for 10 minutes using dry nitrogen stream. The mixed formulation was added to unpurged polypropylene lens molds, and the filled molds were placed in an UV chamber for 15 minutes.

The lenses were removed from the UV-chamber and allowed to cool to room temperature. The lenses were dry released from the molds. Alternatively, the lenses can be wet released from the mold. Dry release or wet release methods are well known to those of ordinary skill in the contact lens art.

Examples 3A and 3B

Hydrogel contact lenses were prepared from formulation examples 3A and 3B. The contact lenses were prepared from a monomer formulation that includes 3-(tris-(trimethylsiloxy)silyl)propyl methacrylate (TRIS), 1-Vinyl-2-pyrrolidinone (NVP), ethylene glycol dimethacrylate (EGDMA), cross-linking agent (2) and diphenyl(2,4,6-trimethylbenzoyl)phosphine oxide (TPO). The amounts of the monomers and cross-linking agent (2) are shown in Table 9:

TABLE 9

| | 3A (wt %) | 3B (wt %) |
|---|---|---|
| TRIS | 79.5 | 45 |
| NVP | 19.0 | 53.5 |
| EGDMA | 0.5 | 0.5 |
| CROSS-LINKING AGENT (2) | 0.5 | 0.5 |
| TPO | 0.5 | 0.5 |

The monomer formulation mixture was mixed well using magnetic stirrer and then degassed for 10 minutes using dry nitrogen stream. The mixed formulation was added to unpurged polypropylene lens molds, and the filled molds were placed in an UV chamber for 15 minutes.

The lenses were removed from the UV-chamber and allowed to cool to room temperature. The lenses were dry released from the molds. Alternatively, the lenses can be wet released from the mold. Dry release or wet release methods are well known to those of ordinary skill in the contact lens art.

Examples 3C and 3D

Hydrogel contact lenses were prepared from formulation examples 3C and 3D. The contact lenses were prepared from a monomer formulation that includes 3-(tris-(trimethylsiloxy)silyl)propyl methacrylate (TRIS), 1-Vinyl-2-pyrrolidinone (NVP), ethylene glycol dimethacrylate (EGDMA), cross-linking agent (2) and azobisisobutyronitrile (AIBN). The amounts of the monomers and cross-linking agent (2) are shown in Table 10:

TABLE 10

|  | 3C (wt %) | 3D (wt %) |
|---|---|---|
| TRIS | 79.5 | 45 |
| NVP | 19.0 | 53.5 |
| EGDMA | 0.5 | 0.5 |
| CROSS-LINKING AGENT (2) | 0.3 | 0.3 |
| AIBN | 0.7 | 0.7 |

The monomer formulation mixture was mixed well using magnetic stirrer and then degassed for 15 minutes using dry nitrogen stream. The mixed formulation was added to unpurged polypropylene lens molds, and the filled molds were placed in an oven for 15 minutes at 60° C. The oven temperature was ramped up to 90° C. over 2 h at 5° C. per 5 minutes. The molds were then left for 4 h at 90° C.

The lenses were removed from the oven and allowed to cool to room temperature. The lenses were dry released from the molds. Alternatively, the lenses can be wet released from the mold. Dry release or wet release methods are well known to those of ordinary skill in the contact lens art.

Examples 3E and 3F

Hydrogel contact lenses were prepared from each formulation examples 3E and 3F. The contact lenses were prepared from a monomer formulation that includes hydroxyethylmethacrylate (HEMA), 1-Vinyl-2-pyrrolidinone (NVP), ethylene glycol dimethacrylate (EGDMA), cross-linking agent (2) and diphenyl(2,4,6-trimethylbenzoyl)phosphine oxide (TPO). The amounts of the monomers and cross-linking agent (2) are shown in Table 11:

TABLE 11

|  | 3E (wt %) | 3F (wt %) |
|---|---|---|
| HEMA | 79.5 | 45 |
| NVP | 19.0 | 53.5 |
| EGDMA | 0.5 | 0.5 |
| CROSS-LINKING AGENT (2) | 0.5 | 0.5 |
| TPO | 0.5 | 0.5 |

The monomer formulation mixture was mixed well using magnetic stirrer and then degassed for 10 minutes using dry nitrogen stream. The mixed formulation was added to unpurged polypropylene lens molds, and the filled molds were placed in an UV chamber for 15 minutes.

The lenses were removed from the UV-chamber and allowed to cool to room temperature. The lenses were dry released from the molds. Alternatively, the lenses can be wet released from the mold. Dry release or wet release methods are well known to those of ordinary skill in the contact lens art.

Examples 3G and 3H

Hydrogel contact lenses were prepared from each formulation examples 3G and 3H. The contact lenses were prepared from a monomer formulation that includes hydroxyethylmethacrylate (HEMA), 1-Vinyl-2-pyrrolidinone (NVP), ethylene glycol dimethacrylate (EGDMA), cross-linking agent (2) and diphenyl(2,4,6-trimethylbenzoyl)phosphine oxide (TPO). The amounts of the monomers and cross-linking agent (2) are shown in Table 12:

TABLE 12

|  | 3G (wt %) | 3H (wt %) |
|---|---|---|
| HEMA | 79.5 | 45 |
| NVP | 19.0 | 53.5 |
| EGDMA | 0.5 | 0.5 |
| CROSS-LINKING AGENT (2) | 0.5 | 0.5 |
| TPO | 0.5 | 0.5 |

The monomer formulation mixture was mixed well using magnetic stirrer and then degassed for 15 minutes using dry nitrogen stream. The mixed formulation was added to unpurged polypropylene lens molds, and the filled molds were placed in an oven for 15 minutes at 60° C. The oven temperature was ramped up to 90° C. over 2 h at 5° C. per 5 minutes. The molds were then left for 4 h at 90° C.

The lenses were removed from the oven and allowed to cool to room temperature. The lenses were dry released from the molds. Alternatively, the lenses can be wet released from the mold. Dry release or wet release methods are well known to those of ordinary skill in the contact lens art.

Examples 3I and 3J

Hydrogel contact lenses were prepared from each formulation examples 3I and 3J. The contact lenses were prepared from a monomer formulation that includes glycidyl methacrylate (GMMA), 1-Vinyl-2-pyrrolidinone (NVP), ethylene glycol dimethacrylate (EGDMA), cross-linking agent (2) and diphenyl(2,4,6-trimethylbenzoyl)phosphine oxide (TPO). The amounts of the monomers and cross-linking agent (2) are shown in Table 13:

TABLE 13

|  | 3I (wt %) | 3J (wt %) |
|---|---|---|
| GMMA | 79.5 | 45 |
| NVP | 19.0 | 53.5 |
| EGDMA | 0.5 | 0.5 |
| CROSS-LINKING AGENT (2) | 0.5 | 0.5 |
| TPO | 0.5 | 0.5 |

The monomer formulation mixture was mixed well using magnetic stirrer and then degassed for 10 minutes using dry nitrogen stream. The mixed formulation was added to unpurged polypropylene lens molds, and the filled molds were placed in an UV chamber for 15 minutes.

The lenses were removed from the UV-chamber and allowed to cool to room temperature. The lenses were dry released from the molds. Alternatively, the lenses can be wet released from the mold. Dry release or wet release methods are well known to those of ordinary skill in the contact lens art.

Examples 3K and 3L

Hydrogel contact lenses were prepared from formulation examples 3K and 3L. The contact lenses were prepared from a monomer formulation that includes 3-methacryloxy-2-hydroxypropyloxy)propylbis(trimethylsiloxy)-methylsilane (SIGMA), 1-Vinyl-2-pyrrolidinone (NVP), ethylene glycol dimethacrylate (EGDMA), cross-linking agent (2) and diphenyl(2,4,6-trimethylbenzoyl)phosphine oxide (TPO). The amounts of the monomers and cross-linking agent (2) are shown in Table 14:

TABLE 14

|  | 3K(wt %) | 3L (wt %) |
| --- | --- | --- |
| SIGMA | 79.5 | 45 |
| NVP | 19.0 | 53.5 |
| EGDMA | 0.5 | 0.5 |
| CROSS-LINKING AGENT (2) | 0.5 | 0.5 |
| TPO | 0.5 | 0.5 |

The monomer formulation mixture was mixed well using magnetic stirrer and then degassed for 10 minutes using dry nitrogen stream. The mixed formulation was added to unpurged polypropylene lens molds, and the filled molds were placed in an UV chamber for 15 minutes.

The lenses were removed from the UV-chamber and allowed to cool to room temperature. The lenses were dry released from the molds. Alternatively, the lenses can be wet released from the mold. Dry release or wet release methods are well known to those of ordinary skill in the contact lens art.

Examples 3M and 3N

Hydrogel contact lenses were prepared from formulation examples 3M and 3N. The contact lenses were prepared from a monomer formulation that includes 3-methacryloxy-2-hydroxypropyloxy)propylbis(trimethylsiloxy)-methylsilane (SIGMA), 1-Vinyl-2-pyrrolidinone (NVP), ethylene glycol dimethacrylate (EGDMA), cross-linking agent (2) and azobisisobutyronitrile (AIBN). The amounts of the monomers and cross-linking agent (2) are shown in Table 15:

TABLE 15

|  | 3M (wt %) | 3N (wt %) |
| --- | --- | --- |
| SIGMA | 79.5 | 45 |
| NVP | 19.0 | 53.5 |
| EGDMA | 0.5 | 0.5 |
| CROSS-LINKING AGENT (2) | 0.3 | 0.3 |
| AIBN | 0.7 | 0.7 |

The monomer formulation mixture was mixed well using magnetic stirrer and then degassed for 15 minutes using dry nitrogen stream. The mixed formulation was added to unpurged polypropylene lens molds, and the filled molds were placed in an oven for 15 minutes at 60° C. The oven temperature was ramped up to 90° C. over 2 h at 5° C. per 5 minutes. The molds were then left for 4 h at 90° C.

The lenses were removed from the oven and allowed to cool to room temperature. The lenses were dry released from the molds. Alternatively, the lenses can be wet released from the mold. Dry release or wet release methods are well known to those of ordinary skill in the contact lens art.

Examples 4A and 4B

Hydrogel contact lenses were prepared from formulation examples 4A and 4B. The contact lenses were prepared from a monomer formulation that includes 3-(tris-(trimethylsiloxy)silyl)propyl methacrylate (TRIS), 1-Vinyl-2-pyrrolidinone (NVP), ethylene glycol dimethacrylate (EGDMA), cross-linking agent (3) and diphenyl(2,4,6-trimethylbenzoyl)phosphine oxide (TPO). The amounts of the monomers and cross-linking agent (3) are shown in Table 16:

TABLE 16

|  | 4A (wt %) | 4B (wt %) |
| --- | --- | --- |
| TRIS | 79.5 | 45 |
| NVP | 19.0 | 53.5 |
| EGDMA | 0.5 | 0.5 |
| CROSS-LINKING AGENT (3) | 0.5 | 0.5 |
| TPO | 0.5 | 0.5 |

The monomer formulation mixture was mixed well using magnetic stirrer and then degassed for 10 minutes using dry nitrogen stream. The mixed formulation was added to unpurged polypropylene lens molds, and the filled molds were placed in an UV chamber for 15 minutes.

The lenses were removed from the UV-chamber and allowed to cool to room temperature. The lenses were dry released from the molds. Alternatively, the lenses can be wet released from the mold. Dry release or wet release methods are well known to those of ordinary skill in the contact lens art.

Examples 4C and 4D

Hydrogel contact lenses were prepared from formulation examples 4C and 4D. The contact lenses were prepared from a monomer formulation that includes 3-(tris-(trimethylsiloxy)silyl)propyl methacrylate (TRIS), 1-Vinyl-2-pyrrolidinone (NVP), ethylene glycol dimethacrylate (EGDMA), cross-linking agent (3) and azobisisobutyronitrile (AIBN). The amounts of the monomers and cross-linking agent (3) are shown in Table 17:

TABLE 17

|  | 4C (wt %) | 4D (wt %) |
| --- | --- | --- |
| TRIS | 79.5 | 45 |
| NVP | 19.0 | 53.5 |
| EGDMA | 0.5 | 0.5 |
| CROSS-LINKING AGENT (3) | 0.3 | 0.3 |
| AIBN | 0.7 | 0.7 |

The monomer formulation mixture was mixed well using magnetic stirrer and then degassed for 15 minutes using dry nitrogen stream. The mixed formulation was added to unpurged polypropylene lens molds, and the filled molds were placed in an oven for 15 minutes at 60° C. The oven temperature was ramped up to 90° C. over 2 h at 5° C. per 5 minutes. The molds were then left for 4 h at 90° C.

The lenses were removed from the oven and allowed to cool to room temperature. The lenses were dry released from the molds. Alternatively, the lenses can be wet released from the mold. Dry release or wet release methods are well known to those of ordinary skill in the contact lens art.

Examples 4E and 4F

Hydrogel contact lenses were prepared from each formulation examples 4E and 4F. The contact lenses were prepared from a monomer formulation that includes hydroxyethylmethacrylate (HEMA), 1-Vinyl-2-pyrrolidinone (NVP), ethylene glycol dimethacrylate (EGDMA), cross-linking agent (3) and diphenyl(2,4,6-trimethylbenzoyl)phosphine oxide (TPO). The amounts of the monomers and cross-linking agent (3) are shown in Table 18:

TABLE 18

|  | 4E (wt %) | 4F (wt %) |
|---|---|---|
| HEMA | 79.5 | 45 |
| NVP | 19.0 | 53.5 |
| EGDMA | 0.5 | 0.5 |
| CROSS-LINKING AGENT (3) | 0.5 | 0.5 |
| TPO | 0.5 | 0.5 |

The monomer formulation mixture was mixed well using magnetic stirrer and then degassed for 10 minutes using dry nitrogen stream. The mixed formulation was added to unpurged polypropylene lens molds, and the filled molds were placed in an UV chamber for 15 minutes.

The lenses were removed from the UV-chamber and allowed to cool to room temperature. The lenses were dry released from the molds. Alternatively, the lenses can be wet released from the mold. Dry release or wet release methods are well known to those of ordinary skill in the contact lens art.

Examples 4G and 4H

Hydrogel contact lenses were prepared from each formulation examples 4G and 4H. The contact lenses were prepared from a monomer formulation that includes hydroxyethylmethacrylate (HEMA), 1-Vinyl-2-pyrrolidinone (NVP), ethylene glycol dimethacrylate (EGDMA), cross-linking agent (3) and diphenyl(2,4,6-trimethylbenzoyl)phosphine oxide (TPO). The amounts of the monomers and cross-linking agent (3) are shown in Table 19:

TABLE 19

|  | 4G (wt %) | 4H (wt %) |
|---|---|---|
| HEMA | 79.5 | 45 |
| NVP | 19.0 | 53.5 |
| EGDMA | 0.5 | 0.5 |
| CROSS-LINKING AGENT (3) | 0.5 | 0.5 |
| TPO | 0.5 | 0.5 |

The monomer formulation mixture was mixed well using magnetic stirrer and then degassed for 15 minutes using dry nitrogen stream. The mixed formulation was added to unpurged polypropylene lens molds, and the filled molds were placed in an oven for 15 minutes at 60° C. The oven temperature was ramped up to 90° C. over 2 h at 5° C. per 5 minutes. The molds were then left for 4 h at 90° C.

The lenses were removed from the oven and allowed to cool to room temperature. The lenses were dry released from the molds. Alternatively, the lenses can be wet released from the mold. Dry release or wet release methods are well known to those of ordinary skill in the contact lens art.

Examples 4I and 4J

Hydrogel contact lenses were prepared from each formulation examples 4I and 4J. The contact lenses were prepared from a monomer formulation that includes glycidyl methacrylate (GMMA), 1-Vinyl-2-pyrrolidinone (NVP), ethylene glycol dimethacrylate (EGDMA), cross-linking agent (3) and diphenyl(2,4,6-trimethylbenzoyl)phosphine oxide (TPO). The amounts of the monomers and cross-linking agent (3) are shown in Table 20:

TABLE 20

|  | 4I (wt %) | 4J (wt %) |
|---|---|---|
| GMMA | 79.5 | 45 |
| NVP | 19.0 | 53.5 |
| EGDMA | 0.5 | 0.5 |
| CROSS-LINKING AGENT (2) | 0.5 | 0.5 |
| TPO | 0.5 | 0.5 |

The monomer formulation mixture was mixed well using magnetic stirrer and then degassed for 10 minutes using dry nitrogen stream. The mixed formulation was added to unpurged polypropylene lens molds, and the filled molds were placed in an UV chamber for 15 minutes.

The lenses were removed from the UV-chamber and allowed to cool to room temperature. The lenses were dry released from the molds. Alternatively, the lenses can be wet released from the mold. Dry release or wet release methods are well known to those of ordinary skill in the contact lens art.

Examples 4K and 4L

Hydrogel contact lenses were prepared from formulation examples 4K and 4L. The contact lenses were prepared from a monomer formulation that includes 3-methacryloxy-2-hydroxypropyloxy)propylbis(trimethylsiloxy)-methylsilane (SIGMA), 1-Vinyl-2-pyrrolidinone (NVP), ethylene glycol dimethacrylate (EGDMA), cross-linking agent (3) and diphenyl(2,4,6-trimethylbenzoyl)phosphine oxide (TPO). The amounts of the monomers and cross-linking agent (3) are shown in Table 21:

TABLE 21

|  | 4K (wt %) | 4L (wt %) |
|---|---|---|
| SIGMA | 79.5 | 45 |
| NVP | 19.0 | 53.5 |
| EGDMA | 0.5 | 0.5 |
| CROSS-LINKING AGENT (3) | 0.5 | 0.5 |
| TPO | 0.5 | 0.5 |

The monomer formulation mixture was mixed well using magnetic stirrer and then degassed for 10 minutes using dry nitrogen stream. The mixed formulation was added to unpurged polypropylene lens molds, and the filled molds were placed in an UV chamber for 15 minutes.

The lenses were removed from the UV-chamber and allowed to cool to room temperature. The lenses were dry released from the molds. Alternatively, the lenses can be wet released from the mold. Dry release or wet release methods are well known to those of ordinary skill in the contact lens art.

Examples 4M and 4N

Hydrogel contact lenses were prepared from formulation examples 4M and 4N. The contact lenses were prepared from a monomer formulation that includes 3-methacryloxy-2-hydroxypropyloxy)propylbis(trimethylsiloxy)-methylsilane (SIGMA), 1-Vinyl-2-pyrrolidinone (NVP), ethylene glycol dimethacrylate (EGDMA), cross-linking agent (3) and azobisisobutyronitrile (AIBN). The amounts of the monomers and cross-linking agent (3) are shown in Table 22:

TABLE 22

|  | 4M (wt %) | 4N (wt %) |
|---|---|---|
| SIGMA | 79.5 | 45 |
| NVP | 19.0 | 53.5 |
| EGDMA | 0.5 | 0.5 |
| CROSS-LINKING AGENT (3) | 0.3 | 0.3 |
| AIBN | 0.7 | 0.7 |

The monomer formulation mixture was mixed well using magnetic stirrer and then degassed for 15 minutes using dry nitrogen stream. The mixed formulation was added to unpurged polypropylene lens molds, and the filled molds were placed in an oven for 15 minutes at 60° C. The oven temperature was ramped up to 90° C. over 2 h at 5° C. per 5 minutes. The molds were then left for 4 h at 90° C.

The lenses were removed from the oven and allowed to cool to room temperature. The lenses were dry released from the molds. Alternatively, the lenses can be wet released from the mold. Dry release or wet release methods are well known to those of ordinary skill in the contact lens art.

This written description uses examples to disclose the invention, including the best mode, and also to enable any person skilled in the art to make and use the invention. Many modifications of the exemplary embodiments of the invention disclosed above will readily occur to those skilled in the art. Accordingly, the invention is to be construed as including all structure and methods that fall within the scope of the appended claims. Unless otherwise specified, the recitation of a genus of elements, materials or other components, from which an individual component or mixture of components can be selected, is intended to include all possible subgeneric combinations of the listed components and mixtures thereof.

We claim:

1. A compound of formula I:

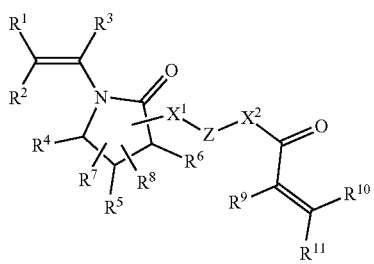

(I)

$R^1$-$R^{11}$ are the same or different, and are each independently selected from H, halo, hydroxyl, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, a substituted or unsubstituted heteroaromatic group, or $NR^a R^b$, wherein $R^a$ and $R^b$ are the same or different, and are independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group;

$X^1$ is selected from $NR^a$, $NR^a C(O)$, $OC(O)NR^a$, $NR^a C(O)O$, $NR^a C(O)NH$, $NHC(O)NR^a$, $OC(O)$, $NHC(O)NHZ_0$—NH—C(O)NH, $OC(O)NHZ_0$—NH—C(O)O, $OC(O)NHZ_0$—NH—C(O)NH, or $NHC(O)NHZ_0$—NH—C(O)O; where $Z_0$ is a linear or branched $C_2$-$C_{12}$ alkylene divalent radical, or a $C_5$-$C_7$ cycloaliphatic divalent radical, each of which can optionally include one or more linkages of O, $NR^a$ and C(O);

$X^2$ is selected from a direct bond, a heteroatom, C(O), a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, a substituted or unsubstituted heteroaromatic group, or $NR^a$; and Z is selected from a heteroatom, C(O), a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, a substituted or unsubstituted heteroaromatic group, $NR^a$, or $[SiR^{12}R^{13}O]_w SiR^{12}R^{13}$, wherein $R^{12}$ and $R^{13}$ are the same or different, and are independently selected from H, halo, hydroxyl, amino, a substituted or unsubstituted hydrocarbon group, a substituted or unsubstituted heterogeneous group, a substituted or unsubstituted carbocyclic group, a substituted or unsubstituted heterocyclic group, a substituted or unsubstituted aromatic group, or a substituted or unsubstituted heteroaromatic group, and w is from 0 to 60.

2. The compound of claim 1, wherein $R^1$-$R^{11}$ are the same or different, and are each independently selected from H, halo, hydroxyl, a substituted or unsubstituted hydrocarbon group, or a substituted or unsubstituted heterogeneous group.

3. The compound of claim 2, wherein $R^1$-$R^{11}$ are the same or different, and are each independently selected from H, halo, hydroxyl, a substituted or unsubstituted $C_1$-$C_6$ alkyl, a substituted or unsubstituted $C_1$-$C_6$ alkoxy, or a substituted or unsubstituted $C_1$-$C_6$ alkanol.

4. The compound of claim 2, wherein $R^1$-$R^{11}$ are the same or different, and are each independently selected from H or a substituted or unsubstituted hydrocarbon group.

5. The compound of claim 4, wherein $R^1$-$R^{11}$ are the same or different, and are each independently selected from H or a substituted or unsubstituted alkyl group.

6. The compound of claim 5, wherein $R^1$-$R^{11}$ are the same or different, and are each independently selected from H or a substituted or unsubstituted $C_1$-$C_6$ alkyl.

7. The compound of claim 6, wherein $R^1$-$R^{11}$ are the same or different, and are each independently selected from H or unsubstituted $C_1$-$C_6$ alkyl.

8. The compound of claim 7, wherein $R^1$-$R^{11}$ are the same or different, and are each independently selected from H or methyl.

9. The compound of claim 1, wherein $R^1$, $R^2$, $R^{10}$, and $R^{11}$ are H.

10. The compound of claim 1, wherein $X^2$ is selected from a direct bond, O, $NR^a$, C(O), $C(O)NR^a$, $NR^a C(O)$, $OC(O)NR^a$, $NR^a C(O)O$, $NR^a C(O)NH$, $NHC(O)NR^a$, $C(O)O$, $OC(O)$, $NHC(O)NHZ_0$—NH—C(O)NH, $OC(O)NHZ_0$—NH—C(O)O, $OC(O)NHZ_0$—NH—C(O)NH, or $NHC(O)NHZ_0$—NH—C(O)O; where $Z_0$ is a linear or branched $C_2$-$C_{12}$ alkylene divalent radical, or a $C_5$-$C_7$ cycloaliphatic divalent radical, each of which can optionally include one or more linkages of O, $NR^a$ and C(O).

11. The compound of claim 1, wherein $X^1$ is selected from $NR^a$, $NR^aC(O)$, $NR^aC(O)O$, $OC(O)NR^a$, $NR^aC(O)O$, or $OC(O)$ and $X^2$ is selected from a direct bond, O, $NR^a$, $C(O)$, $C(O)NR^a$, $NR^aC(O)$, $NR^aC(O)$, $OC(O)NR^a$, $NR^aC(O)O$, $C(O)O$, or $OC(O)$.

12. The compound of claim 11, wherein $X^1$ is selected from $NR^a$, $NR^aC(O)$, $NR^aC(O)O$, $OC(O)NR^a$, or $NR^aC(O)O$ and $X^2$ is selected from a direct bond, O, $NR^a$, $C(O)$, $C(O)NR^a$, $NR^aC(O)$, $NR^aC(O)$, $OC(O)NR^a$, $NR^aC(O)O$, $C(O)O$, or $OC(O)$, wherein $R^a$ is selected from H or a substituted or unsubstituted hydrocarbon group.

13. The compound of claim 12, wherein $R^a$ is selected from H or unsubstituted $C_1$-$C_6$ alkyl.

14. The compound of claim 13, wherein $R^a$ is selected from H or methyl.

15. The compound of claim 10, wherein $X^2$ is selected from a direct bond, O, or $NR^a$.

16. The compound of claim 1, wherein Z is selected from a direct bond, a substituted or unsubstituted hydrocarbon group, a substituted or unsubstituted heterogeneous group, or $[SiR^{12}R^{13}O]_w SiR^{12}R_{13}$.

17. The compound of claim 1, wherein Z is selected from a direct bond, a substituted or unsubstituted hydrocarbon group, a substituted or unsubstituted heterogeneous group, or $[SiR^{12}R^{13}O]_w SiR^{12}R^{13}$, wherein $R^{12}$ and $R^{13}$ are the same or different, and are independently selected from $C_1$-$C_4$ alkyl or phenyl, and w is from 0 to 60.

18. The compound of claim 1, wherein Z is selected from a direct bond, or a substituted or unsubstituted hydrocarbon group.

19. The compound of claim 1, wherein Z is selected from a substituted or unsubstituted hydrocarbon group.

20. The compound of claim 19, wherein Z is selected from a substituted or unsubstituted alkyl group.

21. The compound of claim 19, wherein Z is selected from a substituted or unsubstituted $C_1$-$C_{20}$ alkyl.

22. The compound of claim 19, wherein Z is selected from a substituted or unsubstituted $C_1$-$C_6$ alkyl.

23. The compound of claim 19, wherein Z is selected from an unsubstituted $C_1$-$C_6$ alkyl.

24. The compound of claim 1, wherein Z is selected from a substituted or unsubstituted aromatic group.

25. The compound of claim 24, wherein Z is selected from a substituted or unsubstituted phenyl group.

26. The compound of claim 1, wherein Z is selected from a $C_1$-$C_{12}$ unsubstituted or substituted, linear or branched alkylene divalent radical, where each alkylene divalent radical can optionally include one or more linkages of O, $NR^a$, and $C(O)$, an unsubstituted phenylene divalent radical, a $C_5$-$C_7$ cycloaliphatic divalent radical, or a $C_7$-$C_{12}$ arylalkylene divalent radical.

27. The compound of claim 1, wherein the compound is a dual reactive cross-linking agent(s).

28. A composition comprising one or more of the compounds of claim 1.

29. A cross-linking agent comprising one or more of the compounds of claim 1.

30. A biocompatible medical device comprising one or more of the compounds of claim 1.

31. A method of producing biocompatible medical devices(s), the method comprising reacting at least one of the compounds of claim 1 with at least one monomer.

32. A composition comprising at least one (meth)acrylic monomer, at east one vinyl containing monomer and at least one of the compounds of claim 1.

33. The composition of claim 32, wherein the at least one vinyl containing monomer comprises at least one silicone monomer.

34. The composition of claim 33 wherein the silicone monomer is selected from the group consisting of tris-(trimethylsiloxy)-3-methacryloxypropyl methacrylate (Tris), 3-methacryloxy-2-hydroxypropyloxy) propylbis (trimethylsiloxy)-methylsilane (Sigma), or a mixture thereof.

35. The composition of claim 32, wherein the at least one vinyl containing monomer is selected from hydroxyethyl-methacrylate (HEMA), glycidyl methacrylate (GMMA), dimethylacrylamide (DMA), 3-(tris-(trimethylsiloxy)silyl) propyl methacrylate (TRIS), hydroxypropyloxy)propylbis (trimethylsiloxy)-methylsilane (SIGMA), or combinations thereof.

36. The composition of claim 32, wherein the at least one vinyl monomer is selected from N-vinyl-2-pyrrolidone, N-vinyl piperidone, N-vinyl-caprolactam, N-vinylimidazolidone, N-vinylsuccinimide, N-vinylformamide, N-vinyl urea, N-vinylcarbamate, 0-vinyl carbonate, 1-Vinyl-2-pyrrolidinone (NVP) or combinations thereof.

37. The composition of claim 36 wherein the at least one (meth)acrylic monomer includes 4-t-butyl-2-hydroxycyclohexylmethacrylate, and the at least one vinyl monomer includes N-vinyl-2-pyrrolidone.

38. The composition of claim 32, wherein the at least one (meth)acrylic monomer includes a functional monomer selected from the group consisting of carboxybetaines, sulfobetaines and phosphobetaines.

39. The composition of claim 38, wherein the functional monomer is selected from the group consisting of methacryloxy phosphatidyl choline (MPC), N-vinylcarboxy ethyl phosphatidyl choline, 0-vinyl ethyl phosphatidyl choline carbonate, 1-(3-sulfopropyl)-2-vinylpyridinium betaine, and 3-dimethyl(acryloyloxyethyl) ammonium propyl sulfonate.

40. The composition of claim 32, further comprising at least one photoinitiator.

41. The composition of claim 32, further comprising at least one (meth)acrylate cross-linking agent.

42. The composition of claim 35 wherein the Tris, Sigma or the combination thereof is present from about 8% to about 30% by weight.

43. The composition of claim 32, wherein the at least one compound is present from about 0.02% to about 0.4% by weight.

44. A hydrogel polymer prepared from the composition of claim 28.

45. The hydrogel polymer of claim 44, wherein the polymer possesses a water content of at least about 40% by weight.

46. The hydrogel polymer of claim 44, wherein the polymer possesses a modulus of elasticity of at least about 0.30 MPa.

47. A contact lens prepared with the hydrogel polymer of claim 44.

* * * * *